(12) United States Patent
Ancar

(10) Patent No.: US 11,478,328 B2
(45) Date of Patent: *Oct. 25, 2022

(54) SYSTEM AND METHOD FOR CONTROLLING A COLLIMATOR

(71) Applicant: Terry L Ancar, Jefferson, LA (US)

(72) Inventor: Terry L Ancar, Jefferson, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/592,367

(22) Filed: Feb. 3, 2022

(65) Prior Publication Data

US 2022/0151725 A1   May 19, 2022

Related U.S. Application Data

(63) Continuation of application No. 17/237,796, filed on Apr. 22, 2021, now Pat. No. 11,241,295.

(60) Provisional application No. 63/014,703, filed on Apr. 24, 2020.

(51) Int. Cl.
*A61B 5/00*     (2006.01)
*A61B 90/00*    (2016.01)
*A61B 34/20*    (2016.01)
*G01N 23/04*    (2018.01)
*G02B 27/30*    (2006.01)

(52) U.S. Cl.
CPC .............. *A61B 90/37* (2016.02); *A61B 34/20* (2016.02); *G01N 23/043* (2013.01); *G02B 27/30* (2013.01); *A61B 2090/376* (2016.02)

(58) Field of Classification Search
CPC ... A61B 90/37; A61B 34/20; A61B 2090/376; G02B 27/30; G01N 23/043
See application file for complete search history.

(56) References Cited

U.S. PATENT DOCUMENTS 11,241,295 B2 * 2/2022 Ancar .................. A61B 34/20
2018/0249981 A1  9/2018 Johnson et al.

* cited by examiner

*Primary Examiner* — Joel Lamprecht
(74) *Attorney, Agent, or Firm* — Gustavo Marin; Marin Patents LLC

(57) ABSTRACT

X-ray imaging systems and methods comprising, at least, an x-ray source, an x-ray detector, and a collimator assembly. The collimator assembly comprising a computer, a display, a camera, an x-ray source to object (patient) measuring device to measure source to object distance (SOD), and a plurality of metallic barriers used to manipulate a size and shape of X-ray beams, thereby also reducing the volume of irradiated tissue in the patient. The collimator may comprise computer-controlled motorized shutters to admit radiation into the region defined by the adjustable beam-defining components of the collimator of an X-ray apparatus. In some embodiments, the plurality of metallic barriers may be a fixed cone, or a cone comprised of movable plates.

14 Claims, 19 Drawing Sheets

SYSTEM AND METHOD FOR CONTROLLING A COLLIMATOR

CROSS-REFERENCE TO RELATED APPLICATIONS

This application is a continuation of U.S. application Ser. No. 17/237,796 titled, "SYSTEM AND METHOD FOR AUTOMATIC ADJUSTMENT OF FLUOROSCOPIC IMAGING USING A MOTORIZED COLLIMATOR" filed on Apr. 22, 2021, which claims the benefit of, and priority to U.S. provisional application 63/014,703 titled, "SYSTEM AND METHOD FOR FLUOROSCOPIC IMAGING ALIGNMENT USING A MOTORIZED COLLIMATOR" filed on Apr. 24, 2020, the entire specification of which is incorporated herein by reference.

BACKGROUND OF THE INVENTION

Field of the Art

The disclosure as detailed herein is in the technical field of medicine. More specifically, the present disclosure relates to the technical field of fluoroscopic imaging.

Discussion of the State of the Art

Modern medical facilities, such as hospitals or emergency care facilities, are often large and complex organizations. A medical facility may be organized into various departments or branches that specialize in a particular type of patient care or expertise. For example, a medical facility may have a radiology department that handles various medical imaging tasks such as computed tomography (CT) systems, radiation systems (including both conventional and digital or digitized imaging systems), Magnetic Resonance Imaging (MRI) systems, Positron Emission Tomography (PET) systems, ultrasound systems, nuclear medicine systems, and the like. Such systems provide invaluable tools for identifying, diagnosing, and treating physical conditions and greatly reduce the need for surgical diagnostic intervention. In many instances, these modalities complement one another and offer the physician a range of techniques for imaging particular types of tissue, organs, physiological systems, and so forth. However, patients requiring radiation, for example, must often be transported to the radiology department or even a separate and geographically distant imaging center. This can present additional delays, costs, and inconveniences to the patient and the practitioners.

Digital imaging systems are becoming increasingly widespread for producing digital data that can be reconstructed into useful radiographic images. In one application of a digital imaging system, radiation from a source is directed toward a subject, typically a patient in a medical diagnostic application, and a portion of the radiation passes through the subject and impacts a detector.

A number of devices have been conceived to address the needs to align the X-ray source to the detector of portable and mobile x-ray imaging systems, including developments in portable and mobile units, detectors, and related digital imaging features. For example, US Publication No. 2008/7344305B2 invented by Kuzmanovic, et al, discloses a method and system are providing for performing X-ray diagnostic imaging using a camera image controlled to image a field of view (FOV), that is substantially coincident and coplanar with a radiation footprint or FOV of an X-ray beam radiated towards a patient under examination. The method and system includes acquiring a camera image with a collimated FOV to an X-ray beam FOV before X-ray imaging a patient, displaying the camera image and adjusting the collimation and patient positioning to define the X-ray beam FOV based on the displayed camera image before X-ray imaging the patient. The use of a video camera instead of a light source and mirror to provide a means to visualize the collimated area of the x-ray beam exists in the prior art as described by Kuzmanovic (U.S. Pat. No. 7,344,305 B2). Kuzmanovic teaches the use of a retractable video camera that can be inserted into the central axis of the x-ray beam to create an image through the collimator blades. This image when displayed on a monitor shows the FOV of the collimated X-ray beam area of the patient being exposed. The operator can then adjust the collimator blades to provide the desired area of exposure using the image captured by the camera in real-time. Once the desired area is obtained, the camera is retracted from the beam and an x-ray image can be acquired.

The use of a retractable video camera positioned on the central axis of the x-ray beam does have the advantage that the image it acquires is defined by the position or aperture of the collimator blades, such the acquired images displayed on a monitor are substantially coincident and coplanar with a radiation footprint or FOV of the collimated X-ray beam radiated towards a patient under examination. The problem or disadvantage with this approach is that the user only has the collimated FOV provided by the camera collimated image to assist with visually positioning the radiation beam to the anatomic region being examined. The light source/mirror provides the user the benefit of a projected light field image displayed on the patient that is substantially coincident and coplanar with a radiation footprint or FOV of the collimated X-ray beam radiated towards a patient under examination. The user can view the projected light image and position the lighted image to the region of interest (ROI) with the normally used patient body landmarks to position the projected light field to the anatomic region being examined.

Further, despite advances in the art, there remain significant shortcomings in existing systems used for mobile diagnostic imaging. Current mobile radiography/fluoroscopic imaging systems are cumbersome and expensive. These mobile systems normally incorporate a fixed, mechanical C-arm, or other mechanical configuration which connects the radiation source and the detector to one another, in order to mechanically fix the detector relative to the Radiation source to prevent misalignment outside of normally government-regulated, pre-determined tolerances. In addition, the spatial location of the detector is not always known relative to the Radiation source, as is the case in fixed, permanent digital radiography/fluoroscopic (DR) imaging systems. Especially when the subject to be imaged is very fragile or largely immobile, the need continues to exist for mobile systems which comply with applicable regulations.

Further, systems known in the art use of a retractable video camera positioned on the central axis of the x-ray beam to display acquired images on a monitor that are substantially coincident and coplanar with a radiation footprint or FOV of the collimated X-ray beam radiated towards a patient under examination. A disadvantage with this approach is that the user only has the collimated FOV provided by the camera collimated image to assist with visually positioning the radiation beam to the anatomic region being examined. A further disadvantage of systems known in the art comprising a light source and mirror system is that they must provide protection for a larger area with metal barriers (that is, the larger area to accommodate the light source and mirror) in the t. A larger head unit results in a heavy top portion of a portable radiation system creating high center of gravity resulting in a cumbersome and potentially dangerous situation when in movement.

What is needed in the art are systems and methods for providing an image that is substantially within the same FOV of the patient as the calculated active area of the detector and an overlay shaded area within the image that is substantially within the same FOV of the radiation beam with the shaded area representing a collimated area of the collimator based on shutter position, the shaded area further operable to change position based on interaction from an interactive display and have the collimator shutters respond to changes in position while creating an environment whereby a smaller area within the head unit is present, to reduce the amount and weight of the metal barrier.

SUMMARY OF THE INVENTION

Accordingly, the inventor has conceived and reduced to practice, in a preferred embodiment of the invention, an X-ray imaging system comprising, at least, an x-ray source, an x-ray detector, and a collimator assembly. The collimator assembly comprises, at least, a computer, a display, a camera, an x-ray source to object (patient) measuring device to measure source to object distance (SOD), and a plurality of metallic barriers controllable via the network, with an adjustable aperture used to manipulate a size, shape, and location of X-ray beams, thereby also reducing the volume of irradiated tissue in the patient. The collimator may comprise computer-controlled motorized shutters to define a collimated area that admits radiation into the region defined by the adjustable beam-defining components of the collimator of an X-ray apparatus. In some embodiments, the plurality of metallic barriers may be a fixed cone, or a cone comprised of movable plates.

Filtration and collimation of the X-ray beam are important safety measures. In a preferred embodiment, the camera may provide an image that is substantially within the same FOV of the patient as the calculated active area of the detector. Further, the camera may provide indicia (for example, overlay a shaded area. Hereinafter the indicia also referred to as shaded area) within the camera image that represent substantially the same FOV as the shutter aperture size and location (also referred to herein as collimated area).

The computer may use the known position and size of the shutter aperture and the SOD information to calculate and adjust a size and position of the shaded area within the camera image of patient with respect to the active area of detector. By viewing the camera images, the operator or clinician (also referred to herein as user) may determine directly, particularly during pre-examination alignment, whether the radiation beam is aligned to the anatomic region that will be irradiated. That is, the camera provides a FOV of the radiation beam overlayed on an image of the patient, wherein the viewer immediately knows if the FOV has changed, or needs to be changed by patient and/or collimator realignment, etc. The method of examination in accordance with an embodiment of the invention is different from conventional patient or alignment imaging, and diagnostic imaging methods. By use of the inventive system and method, the clinician may realize improved patient throughput, reduced patient and/or clinician exposure to unnecessary X-ray exposure, unnecessary discarded images and reduced dose levels overall due to improved collimator adjustment whilst complying with governmental regulations to provide means for visually defining the perimeter of the x-ray field.

According to a preferred embodiment of the invention, the inventive x-ray imaging system comprises an x-ray source for generating and controlling an X-ray beam radiated towards a patient under examination. The X-ray source comprises an X-ray tube, and x-ray collimator assembly. In a preferred embodiment, the collimator assembly comprises, at least, a camera, a computer, a distance measuring device (SOD), and an interactive visual display. The camera may be arranged to image with an adjustable field of view (FOV) at a physical position of the X-ray beam and the patient that is substantially coincident with and at least as large as a maximum radiation pattern footprint or FOV of the radiated X-ray beam. Both the radiated beam, and camera FOV are shaped and/or limited by the collimator computer. The system comprises an X-ray imaging device arranged for receiving the X-ray beam after it has passed through the patient and acquiring latent image frames of a region of interest (ROI) within the patient's anatomy. One or more computers communicatively connected to the X-ray source, X-ray imaging device and collimator computer controls latent image frame acquisition and post-acquisition processing, including controlling the X-ray tube, x-ray imaging device and provides data to the collimator computer to adjust the position and size of the radiation beam FOV and the position and size of the shaded area within the camera image. The image processing chain comprising an image processor that is coupled to the system computer receives the latent image frames from the X-ray imaging device for processing and a display device coupled to the image processing chain displays post-processed image frames as an X-ray diagnostic image of the ROI.

The camera images may be displayed on the visual display during normal imaging operation, or display camera images only when the X-ray system is in a pretest or physical set-up operation, wherein a position and size of the collimator aperture is arranged to constrict the FOV of the X-ray beam and camera shaded area are substantially similarly. In a preferred embodiment, the camera is a video capable camera, and most preferably that the video camera is miniaturized. Of course, a focusing system that is included with the camera to focus the camera FOV such as the available area that could be exposed when the collimator shutters are fully opened and the shaded area within the FOV.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary and are not to be considered as limiting of the scope of the invention or the claims herein in any way.

Figure 12A:
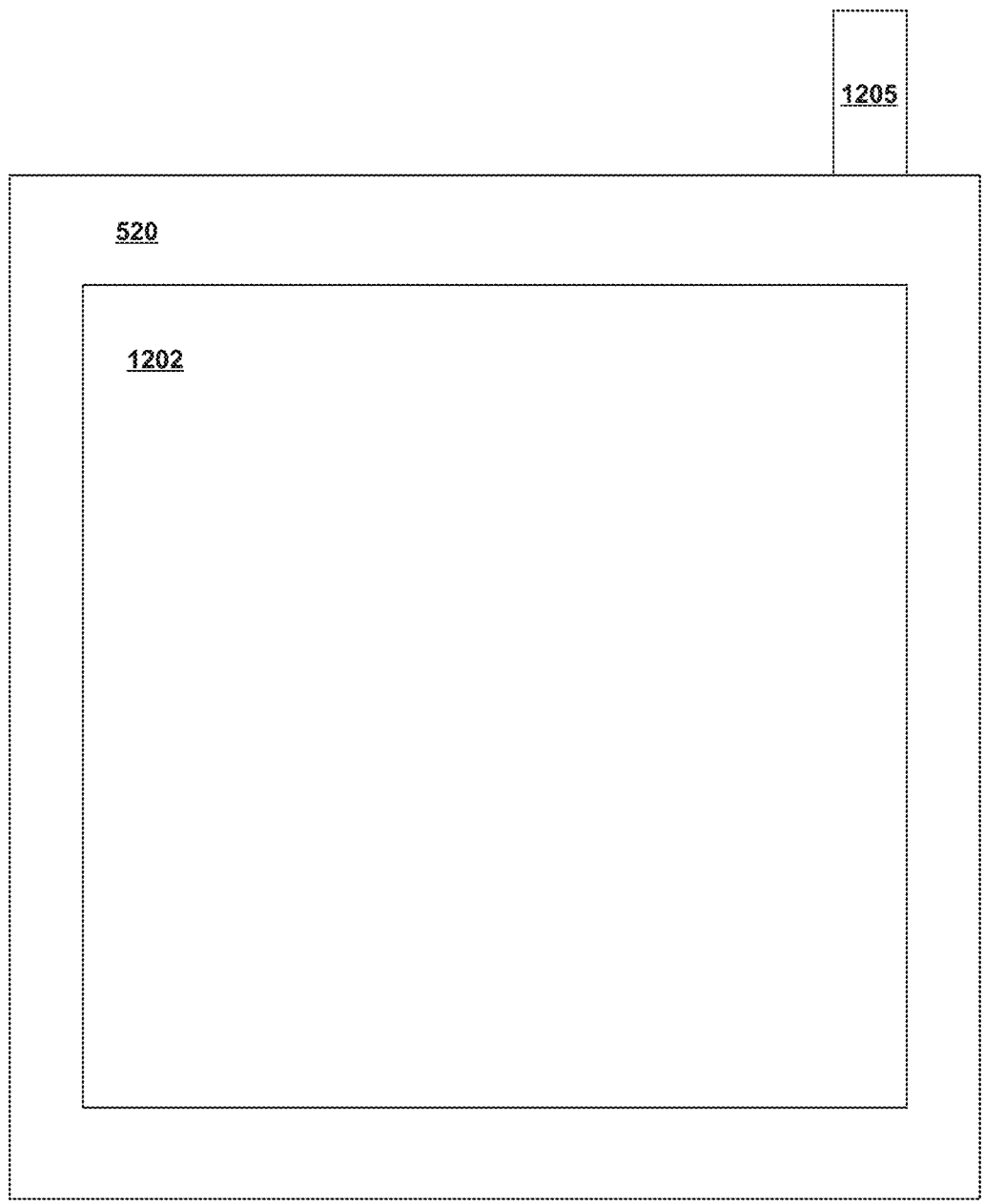
Figure 12B:
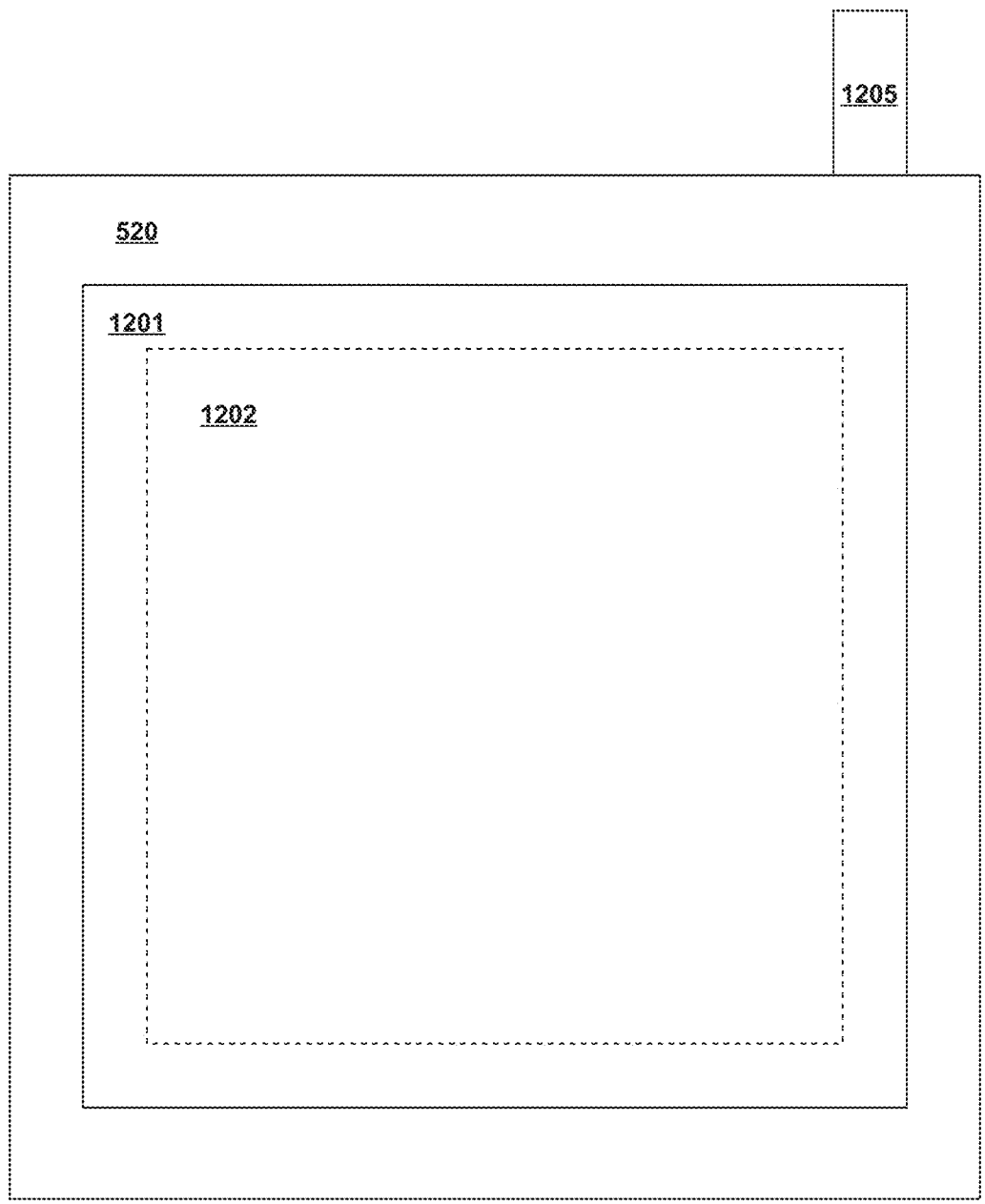
Figure 12C:
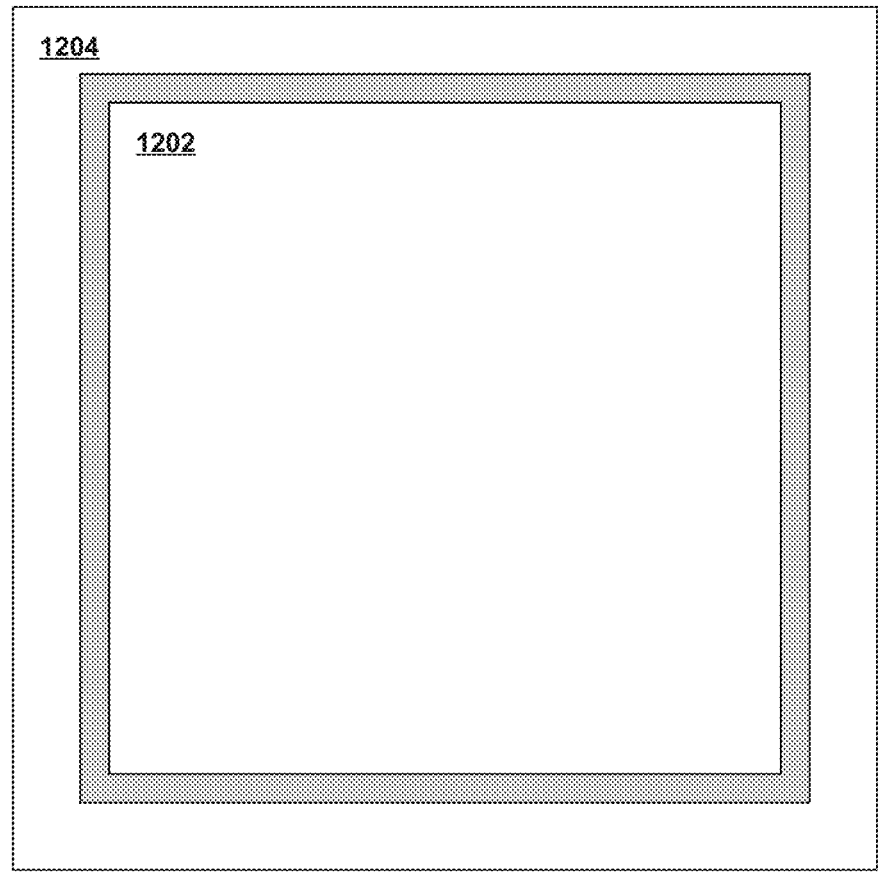

FIG. 12A-C is a block diagram illustrating a portable detector, according to a preferred embodiment of the invention.

DETAILED DESCRIPTION

The inventor has conceived, and reduced to practice, a system and method for fluoroscopic imaging using a motorized collimator.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article.

Similarly, where more than one device or article is described herein, it will be readily apparent that a single device or article may be used in place of the more than one device or article. When a single computer and/or processor is described herein, it will be readily apparent that more than one computer and/or processor, for example, a plurality of network-connected computer and/or plurality of processors within a single computer may be used in place of a single computer. Similarly, where more than one computer and/or processor is described herein, it will be readily apparent that a single computer and/or processor may be used in place of the more than one device or article.

Functions performed by one computer may be performed by another in different, or the same, embodiment.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 1:
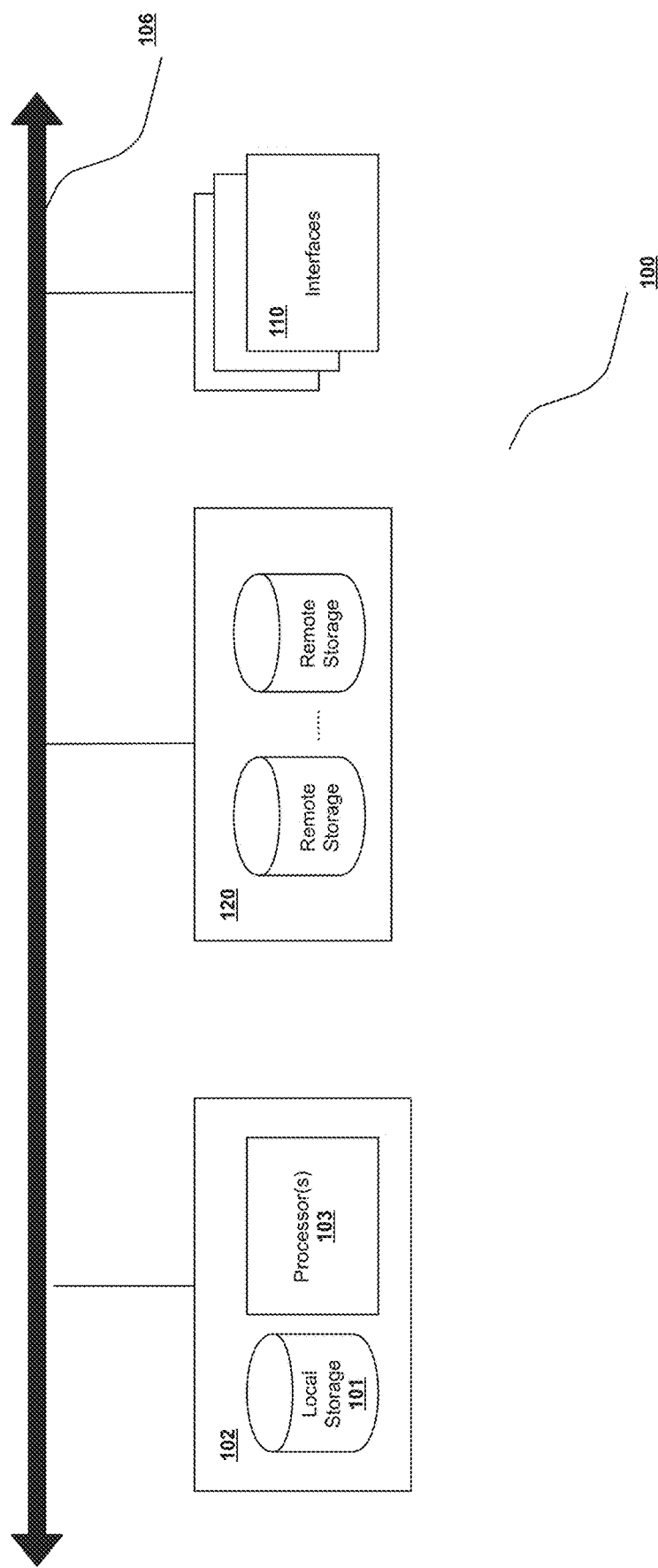
FIG. 1 is a block diagram illustrating an exemplary hardware architecture of a computing device used in an embodiment of the invention.

Referring now to FIG. 1, there is shown a block diagram depicting an exemplary computing device 100 suitable for implementing at least a portion of the features or functionalities disclosed herein. Computing device 100 may be, for example, any one of the computing machines listed in the previous paragraph, or indeed any other electronic device capable of executing software- or hardware-based instructions according to one or more programs stored in memory. Computing device 100 may be adapted to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 100 comprises one or more central processing units (CPU) 102, one or more interfaces 110, and one or more busses 106 (such as a peripheral component interconnect (PCI) bus). When acting under the control of appropriate software or firmware, CPU 102 may be responsible for implementing specific functions associated with the functions of a specifically configured computing device or machine. For example, in at least one embodiment, a computing device 100 may be configured or designed to function as a server system utilizing CPU 102, local memory 101 and/or remote memory 120, and interface(s) 110. In at least one embodiment, CPU 102 may be caused to perform one or more of the different types of functions and/or operations under the control of software modules or components, which for example, may include an operating system and any appropriate applications software, drivers, and the like.

CPU 102 may include one or more processors 103 such as, for example, a processor from one of the Intel, ARM, Qualcomm, and AMD families of microprocessors. In some embodiments, processors 103 may include specially designed hardware such as application-specific integrated circuits (ASICs), electrically erasable programmable read-only memories (EEPROMs), field-programmable gate arrays (FPGAs), and so forth, for controlling operations of computing device 100. In a specific embodiment, a local memory 101 (such as non-volatile random-access memory (RAM) and/or read-only memory (ROM), including for example one or more levels of cached memory) may also form part of CPU 102. However, there are many different ways in which memory may be coupled to system 100. Memory 101 may be used for a variety of purposes such as, for example, caching and/or storing data, programming instructions, and the like. It should be further appreciated that CPU 102 may be one of a variety of system-on-a-chip (SOC) type hardware that may include additional hardware such as memory or graphics processing chips, such as a Qualcomm SNAPDRAGON™ or Samsung EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 110 are provided as network interface cards (NICs). Generally, NICs control the sending and receiving of data packets over a computer network; other types of interfaces 110 may for example support other peripherals used with computing device 100. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (Wi-Fi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 110 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 1 illustrates one specific architecture for a computing device 100 for implementing one or more of the inventions described herein, it is by no means the only device architecture on which at least a portion of the features and techniques described herein may be implemented. For example, architectures having one or any number of processors 103 may be used, and such processors 103 may be present in a single device or distributed among any number of devices. In one embodiment, a single processor 103 handles communications as well as routing computations, while in other embodiments a separate dedicated communications processor may be provided. In various embodiments, different types of features or functionalities may be implemented in a system according to the invention that comprises a client device (such as a tablet device or smartphone running client software) and server systems (such as a server system described in more detail below).

Regardless of network device configuration, the system of the present invention may employ one or more memories or memory modules (such as, for example, remote memory block 120 and local memory 101) configured to store data, program instructions for the general-purpose network operations, or other information relating to the functionality of the embodiments described herein (or any combinations of the above). Program instructions may control execution of or comprise an operating system and/or one or more applications, for example. Memory 120 or memories 101, 120 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a Java™ compiler and may be executed using a Java virtual machine or equivalent, or files containing higher level code that may be executed by the computer using an interpreter (for example, scripts written in Python, Perl, Ruby, Groovy, or any other scripting language).

Figure 2:
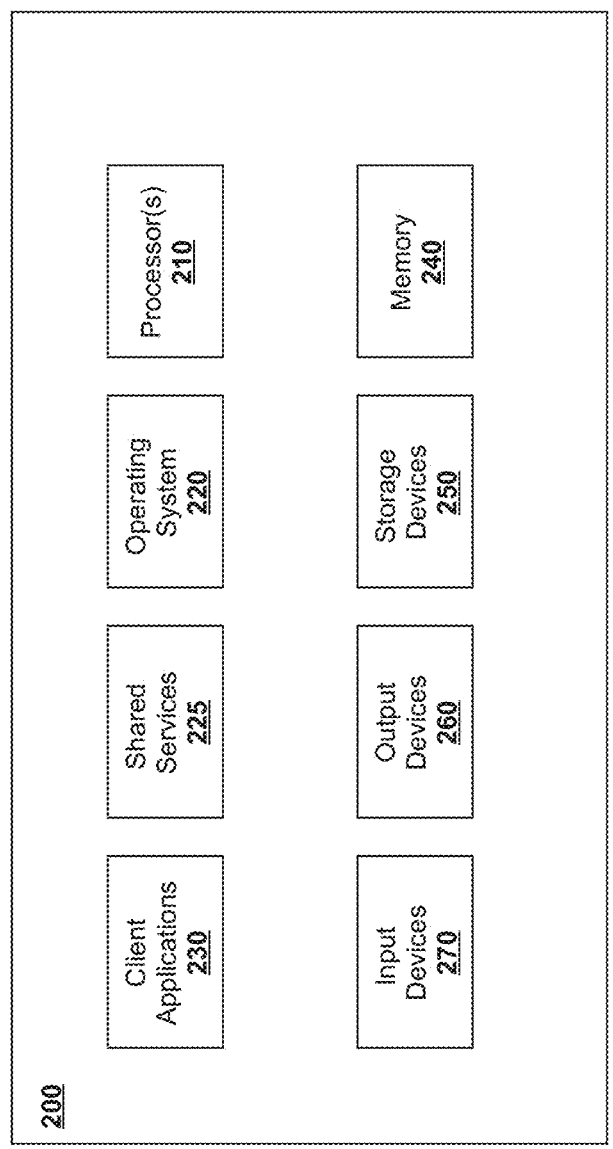
FIG. 2 is a block diagram illustrating an exemplary logical architecture for a client device, according to an embodiment of the invention.

In some embodiments, systems according to the present invention may be implemented on a standalone computing system. Referring now to FIG. 2, there is shown a block diagram depicting a typical exemplary architecture of one or more embodiments or components thereof on a standalone computing system. Computing device 200 comprises processors 210 that may run software that carry out one or more functions or applications of embodiments of the invention, such as for example a client application 230. Processors 210 may carry out computing instructions under control of an operating system 220 such as, for example, a version of Microsoft's WINDOWS™ operating system, Apple's Mac OS/X or iOS operating systems, some variety of the Linux operating system, Google's ANDROID™ operating system, or the like. In many cases, one or more shared services 225 may be operable in system 200 and may be useful for providing common services to client applications 230. Services 225 may for example be WINDOWS™ services, user-space common services in a Linux environment, or any other type of common service architecture used with operating system 210. Input devices 270 may be of any type suitable for receiving user input, including for example a keyboard, touchscreen, microphone (for example, for voice input), mouse, touchpad, trackball, or any combination thereof. Output devices 260 may be of any type suitable for providing output to one or more users, whether remote or local to system 200, and may include for example one or more screens for visual output, speakers, printers, or any combination thereof. Memory 240 may be random-access memory having any structure and architecture known in the art, for use by processors 210, for example to run software. Storage devices 250 may be any magnetic, optical, mechanical, memristor, or electrical storage device for storage of data in digital form (such as those described above, referring to FIG. 1). Examples of storage devices 250 include flash memory, magnetic hard drive, CD-ROM, and/or the like.

Figure 3:
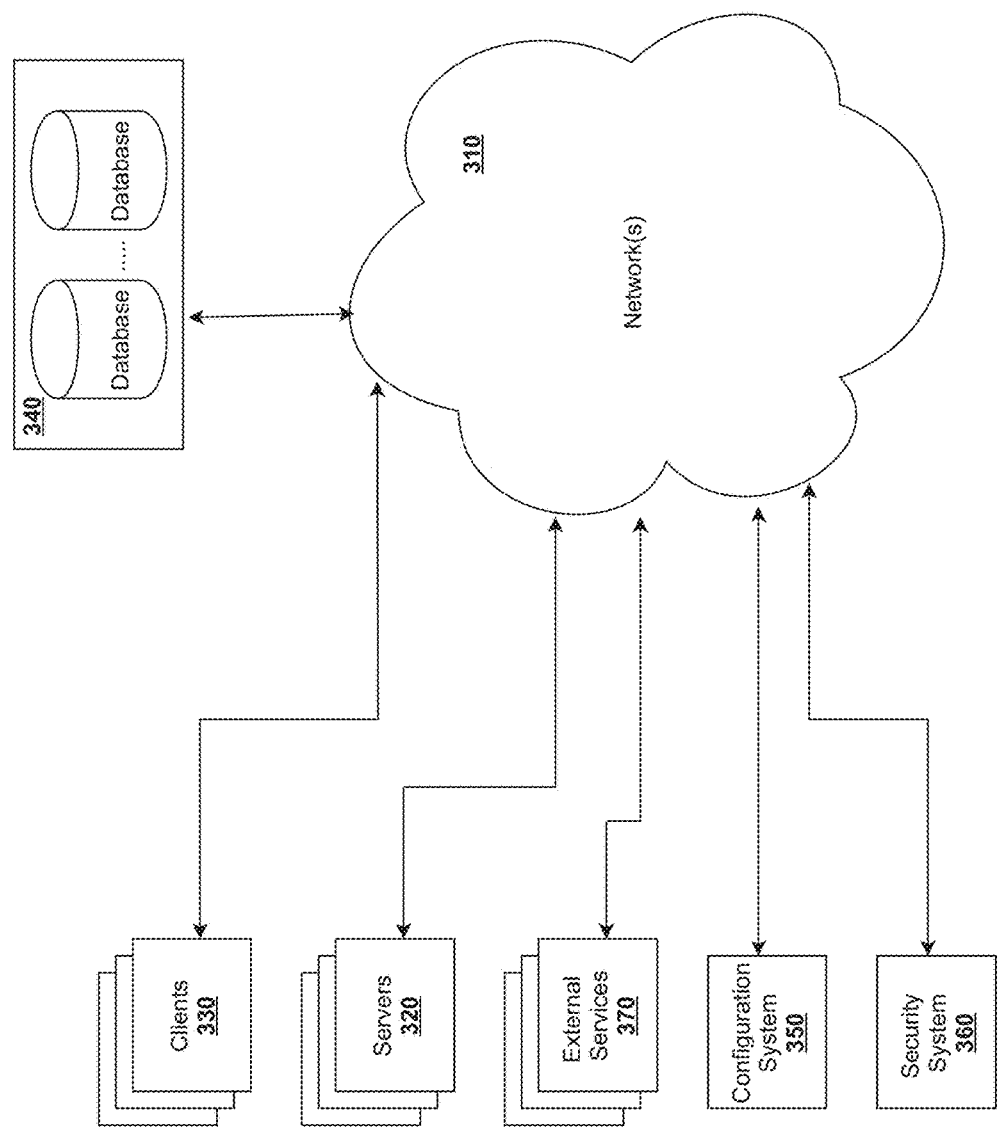
FIG. 3 is a block diagram showing an exemplary architectural arrangement of clients, servers, and external services, according to an embodiment of the invention.

In some embodiments, systems of the present invention may be implemented on a distributed computing network, such as one having any number of clients and/or servers. Referring now to FIG. 3, there is shown a block diagram depicting an exemplary architecture 300 for implementing at least a portion of a system according to an embodiment of the invention on a distributed computing network. According to the embodiment, any number of clients 330 may be provided. Each client 330 may run software for implementing client-side portions of the present invention; clients may comprise a system 200 such as that illustrated in FIG. 2. In addition, any number of servers 320 may be provided for handling requests received from one or more clients 330.

Clients 330 and servers 320 may communicate with one another via one or more electronic networks 310, which may be in various embodiments any of the Internet, a wide area network, a mobile telephony network (such as CDMA or GSM cellular networks), a wireless network (such as Wi-Fi, WiMAX, LTE, and so forth), or a local area network (or indeed any network topology known in the art; the invention does not prefer any one network topology over any other). Networks 310 may be implemented using any known network protocols, including for example wired and/or wireless protocols.

In addition, in some embodiments, servers 320 may call external services 370 when needed to obtain additional information, or to refer to additional data concerning a particular call. Communications with external services 370 may take place, for example, via one or more networks 310. In various embodiments, external services 370 may comprise web-enabled services or functionality related to or installed on the hardware device itself. For example, in an embodiment where client applications 230 are implemented on a smartphone or other electronic device, client applications 230 may obtain information stored in a server system 320 in the cloud or on an external service 370 deployed on one or more of a particular enterprise's or user's premises.

In some embodiments of the invention, clients 330 or servers 320 (or both) may make use of one or more specialized services or appliances that may be deployed locally or remotely across one or more networks 310. For example, one or more databases 340 may be used or referred to by one or more embodiments of the invention. It should be understood by one having ordinary skill in the art that databases 340 may be arranged in a wide variety of architectures and using a wide variety of data access and manipulation means. For example, in various embodiments one or more databases 340 may comprise a relational database system using a structured query language (SQL), while others may comprise an alternative data storage technology such as those referred to in the art as "NoSQL" (for example, Hadoop Cassandra, Google BigTable, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 360 and configuration systems 350. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 360 or configuration system 350 or approach is specifically required by the description of any specific embodiment.

Figure 4:
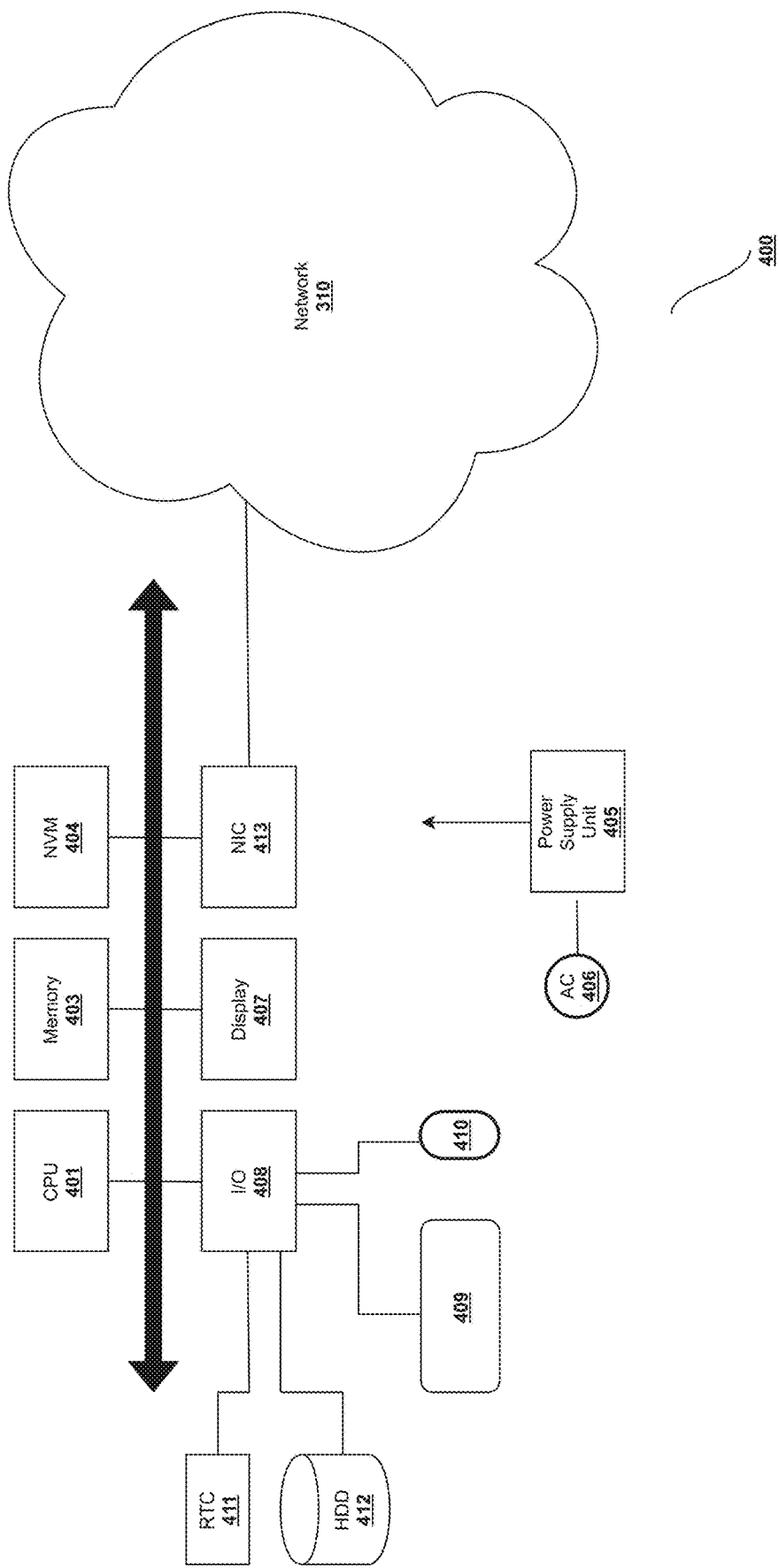
FIG. 4 is another block diagram illustrating an exemplary hardware architecture of a computing device used in various embodiments of the invention.

FIG. 4 shows an exemplary overview of a computer system 400 as may be used in any of the various locations throughout the system. It is exemplary of any computer that may execute code to process data. Various modifications and changes may be made to computer system 400 without departing from the broader spirit and scope of the system and method disclosed herein. CPU 401 is connected to bus 402, to which bus is also connected memory 403, nonvolatile memory 404, display 407, I/O unit 408, and network interface card (NIC) 413. I/O unit 408 may, typically, be connected to keyboard 409, pointing device 410, hard disk 412, and real-time clock 411. NIC 413 connects to network 414, which may be the Internet or a local network, which local network may or may not have connections to the Internet. Also shown as part of system 400 is power supply unit 405 connected, in this example, to ac supply 406. Not shown are batteries that could be present, and many other devices and modifications that are well known but are not applicable to the specific novel functions of the current system and method disclosed herein. It should be appreciated that some or all components illustrated may be combined, such as in various integrated applications (for example, Qualcomm or Samsung SOC-based devices), or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

Conceptual Architecture

Figure 5:
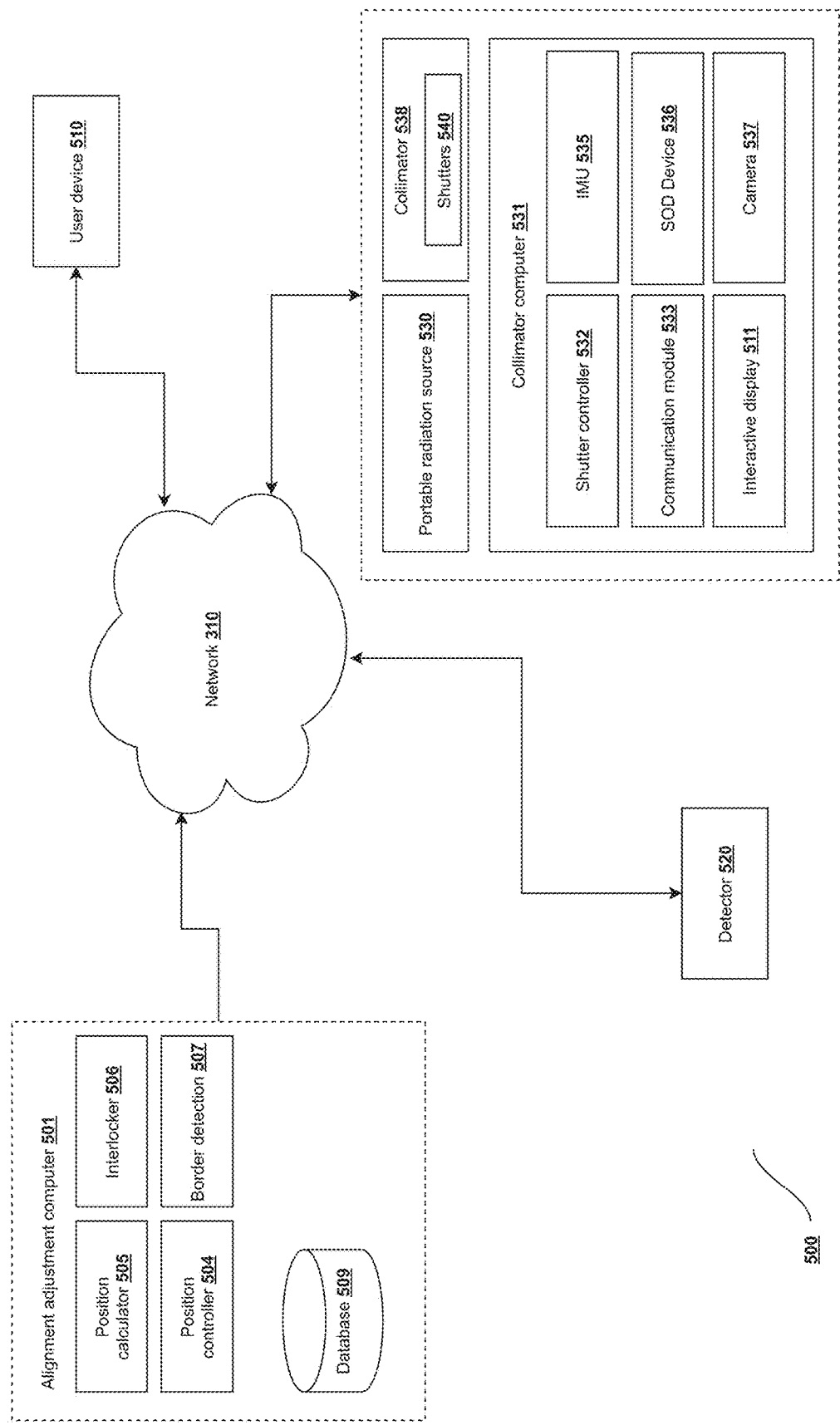
FIG. 5 is a block diagram illustrating an exemplary conceptual architecture of an alignment adjustment system, according to a preferred embodiment of the invention.

FIG. 5 is a block diagram illustrating an exemplary conceptual architecture of an alignment adjustment system, according to a preferred embodiment of the invention.

According to the embodiment, alignment adjustment system 500 comprises alignment adjustment computer 501 comprising a plurality of components each comprising at least a plurality of programming instructions, the programming instructions stored in memory 240 that when executed by one or more processors 210, cause one or more processor 210 to perform operations disclosed herein. Functions described by system 500 may be on one processing platform or computer or may be distributed across a plurality of computing platforms and/or processors.

In an embodiment, alignment adjustment computer 501 may comprise, position controller 504, interlocker 506, position calculator 505, border detection module 507, user interface 511, and database 509. Further, alignment adjustment computer 501 may communicate with detector 520 (also herein referred to as detector 147 referring to FIG. 12B), portable radiation source 530 (also referred to herein as radiation source 18), one or more user devices 510, collimator 538, and collimator computer 531, via network 310. Further, collimator computer 531 may comprise shutter controller 532, IMU 535, communication module 533, SOD device 536, display 534, and camera 537.

In a preferred embodiment, portable detector 520 comprises a surface to convert radiation striking the detector 520 from radiation source 530 to light photons. The detector is divided into an array of discrete picture elements or pixels to encode output signals based upon the quantity or intensity of the radiation impacting each pixel region. Because the radiation intensity is altered as the radiation passes through the subject, images may be reconstructed based upon the output signals to provide a projection of tissues and other features similar to those available through conventional photographic film techniques.

In use, the signals generated at pixel locations of the detector 520 are digitized. The digital values are transmitted to processing circuitry where they are filtered, scaled, and further processed to produce an image data set. The data set may then be used to reconstruct a resulting image and the image may be displayed on an output device.

In a preferred embodiments, collimator 538 comprises a device that adjusts a beam size to a desired size for imaging a desired area through a collimated area created by shutter positions. Collimator 538 may preferably comprise collimator shutter blades 1101-1104 (referring to FIG. 11A). Collimator shutter blades 1101-1104 function as part of the collimator 538 as an aperture to allow narrowing and directionally control radiation beams for imaging purposes defining the collimated area. Though only four shutters are shown in the exemplary embodiment, any number of collimator shutters may be used, for example, overlapping leaves.

In some embodiments, a collimator hole in shutter blades comprises an embodiment where the collimator may have holes in the shutter blades that may be a source of alignment radiation beams (that is, an intensity of radiation used to measure alignment). In a preferred embodiment, an incomplete closure of the collimator shutter blades 1101-1104 comprise a collimated area. In some embodiments, a positioning aperture plate comprises one or more configurable plates to limit most or all exit radiation from the radiation source, except for those through alignment beam holes to generate a radiation alignment radiation beams, or any object placed between the radiation source and the portable detector to perform an alignment exposure. In some embodiments, a low dose system may comprise an embodiment where radiation beams are created by a portable radiation system capable of emitting a low dose alignment radiation beams.

During calibration of system 500 radiation source 530 may be placed within a known acceptable spatial distance of a portable detector 520 for calibration. Radiation beams are released towards the portable detector 520 at the acceptable or preconfigured distance to establish a reference image to be used in future processes for calculating source image distance (SID), skew and rotation. it should be appreciated by one with ordinary skill in the art that by capturing a reference image, while calibrating, with known detector sizes, known distances (for example, during initial setup of system 500), then when future images are captured by portable detector 520 (for example, in a diagnostic imaging environment such as a treatment room), the subsequent images will be usable by the computer to compare images to determine alignment, skew, rotation, and the like. The radiation beams may comprise radiation that is emitted through an aperture created by shutter blades 1101-1104 for calibration. In some embodiments, a calibration image is then created with a portable detector 520. The calibration image can then be used to determine a size of an examination area, a skewed or rotated position of portable detector 520, relative to the calibration image or within a predetermined tolerance for subsequent radiation procedures. Further by using preconfigured calibration data, a calculation of virtual border representation, by collimator computer 531.

In a preferred embodiment, database 509 comprises data structures and systems to hold information for configuring system 500 including, but not limited to, patient profile, patient attributes such as dimension, weight, etc., reference image data, information received by a user such as selecting and/or configuring one or more sizes of one or more detectors. System 500 may use information from database 509 (for example, a preconfigured portable detector size), to programmatically compute a virtual border (for example 802 referring to FIG. 8B) stored in the computer memory that represents borders around a detector. It should be noted that even though the term patient is used herein, any object can be used for radiation procedures.

In operation, camera 537 may be installed on, within, or in close proximity to collimator 538. In an embodiment, camera 537 may transmit a plurality of images or video to user interface 511, that is, real-time and live video images of a patient as seen from the perspective of collimator 538, a FOV of the patient as the calculated active area of the detector, or other images. Further, camera 537 may also provide a shaded, blurred, hash or any other pattern on the video images as means to view a specific area within a video or still image, for example, the shaded area representing a perspective of collimator 538 comprising an area for fluoroscopic and/or radiographic imaging and present the shaded area to display 511. The patterned art of the video image may clearly define a size and a location of one or more radiation beams, as would be received from detector 530 during a procedure. According to the embodiment, collimator 538 may further consist of a distance measuring device, represented by SOD device 536, to accurately measure a distance between collimator 538 and the patient. For example, SOD device 536 may comprise of a laser device or ultrasound measuring device.

In some embodiments, collimator computer 531 may receive the video images from camera 537 and apply video cropping and trimming procedures to the video images, for example, as defined by user interface 511 using gestures, as is known in the art, to define the shaded area (or the entire image) by user gesture commands that may control a size, orientation, and position to establish positioning data. There are many types of gestures, from the simple single-touch swipe gesture, pinch-and-zoom gesture, to the more complex multi-touch twist gesture, where the touch points may move in different directions. This may be performed to adjust an outer perimeter of the video images with respect to the size of detector 520, at a distance measured by SOD device 536. Further, collimator computer 531 may adjust the crop and trim of the shaded area within the video images, so that only the size and the location of a shutter aperture size of shutters 540 (that is, shutters 1101-1104 referring to FIG. 11B), correspond to the shaded area. Once established, positioning data may be sent to position controller 504.

In an embodiment, position controller 504 (or in some embodiments, display 511) may send positioning data to collimator computer 531, which may be used, by shutter controller 532, to adjust the shutter aperture size. The shutter aperture size may then be adjusted by the one or more motorized shutters 540 (also referred to herein as shutters 1101-1104 referring to FIG. 11A). This may be done to ensure that the size and location of the shaded area within the video images may have a similar field of view (FOV) as the shutter aperture, with respect to the video images from camera 537 with substantially the same size as the detector 520. In one embodiment, the video images of the patient and shaded area within the video images may be displayed on display 511.

In some embodiments, collimator computer 531 may analyze each frame of acquired image data to determine if an exposed area of detector 520 activates one or more borders of detector 520 (i.e., a predefined plurality of pixels are activated by radiation, for example, on one or more outer edge of detector 520 as depicted by area 1201 referring to FIGS. 12B and 12C). If a border area is not activated by radiation, then alignment adjustment computer 501 may continue with image acquisition and the next frame of image may be acquired. However, if radiation is in a vicinity to (that is, approaching a border) or activates any of the one or more border pixels of detector 520, collimator computer 531 may attempt to reposition the radiation beam towards the center of detector 520 by moving one or more of shutters 540. Further, in case the repositioning of the radiation beam does not satisfy the border infringement, e.g., due to the mechanical limitations of the collimator 538, a radiation exposure termination (also referred to herein as interlock) command may be sent by collimator computer 531. Accordingly, interlocker 506 may engage a radiation interlock to stop radiation from portable radiation source 530 and in some embodiments, an alert may be sent to alignment adjustment computer 501, collimator computer 531, user device 510, or a combination thereof. Further, an error message may be displayed at user interface 511 comprising the last received frame of the image data. The error message may further contain instructions to readjust the position of the portable radiation source 530 or detector 520 and reattempt the alignment process.

Detailed Description of Exemplary Embodiments

Figure 6A:
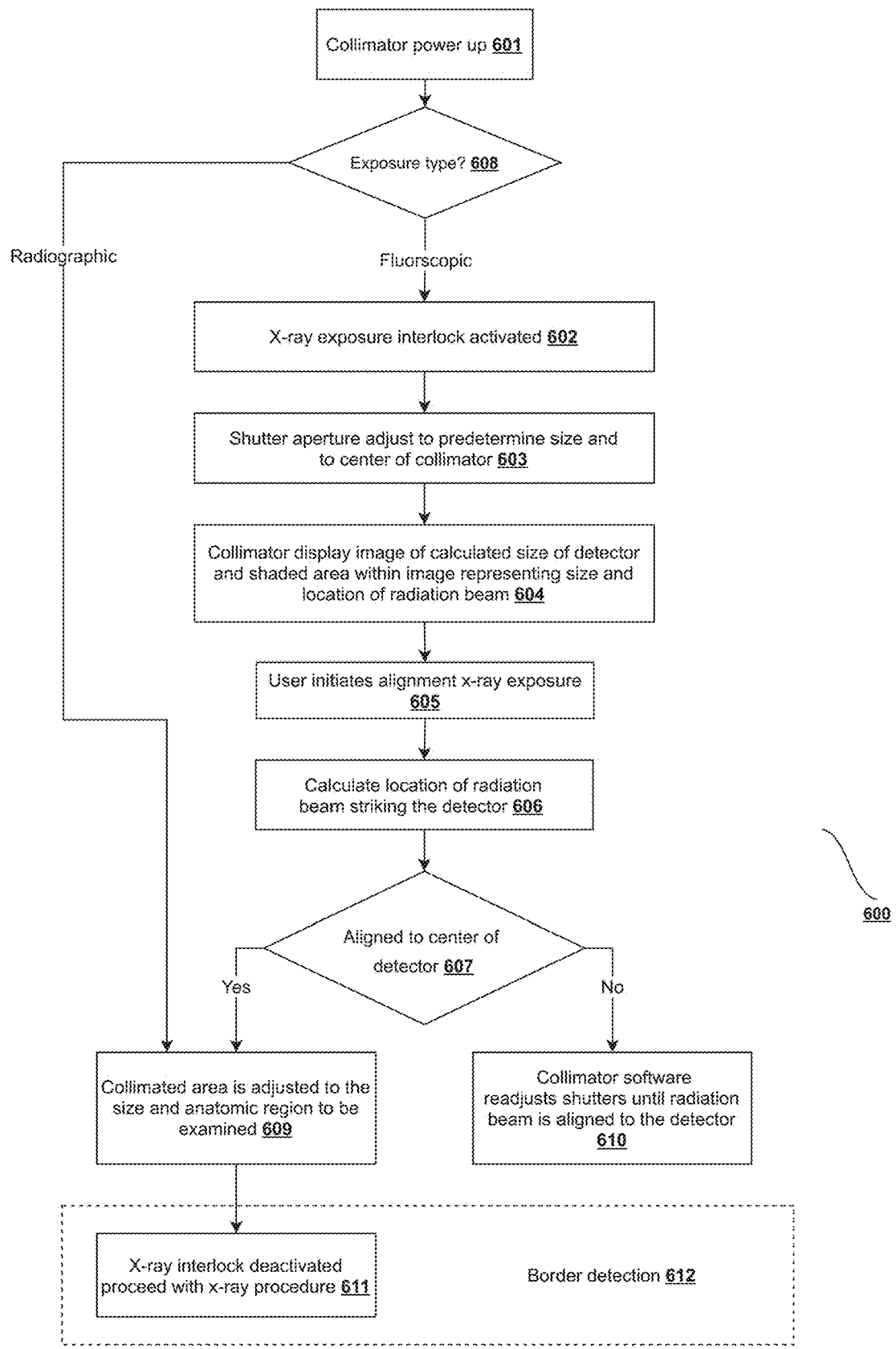
FIG. 6A is a flow diagram illustrating a method for automatically adjusting collimator shutters, according to a preferred embodiment of the invention.

FIG. 6A a flow diagram illustrating a method for adjusting collimator shutters, according to a preferred embodiment of the invention. According to the embodiment, method 600 starts at step 601, wherein collimator 538 may be powered up. Accordingly, a first alignment process to align portable radiation source 530 and detector 520 may have been initiated. In a next step 608, collimator computer 531 may determine a type of exposure that is to be performed. In an embodiment, collimator computer 531 may determine the type of exposure based on receiving input from display 511 or from a network-connected workstation computer. The selection obtained from user device 510, in an example, may be one of a radioscopic imaging process or a fluoroscopic imaging process.

Referring again to FIG. 6A, in case that it is determined that a fluoroscopic imaging process has been selected, in a next step 602, communication module 533 may send an x-ray exposure interlock signal to interlocker 506. In response to receiving the signal, interlocker 506 may activate the x-ray exposure interlock to prevent diagnostic (or procedure) radiation from radiation source 530. That is, alignment x-ray exposure may still be permitted. In a next step 603, shutter controller 532 may adjust shutter aperture of shutters 540 of collimator 538. The shutter aperture of shutters 540 may be adjusted to a predetermined size and to a center of collimator 538.

In a next step 604, interactive display 511 may display an image of calculated size of detector 520, and an image of the patient or object being examined. Further, Interactive display 511 may also display a shaded area within the image, wherein the shaded area may represent a size and a location of a collimated area representing where radiation may be received by a patient (that is, the object within the image). For example, area 811 referring to FIG. 8D, from portable radiation source 530. In some embodiments, the shaded area within the image may represent a size and a location of a collimated area representing where radiation may be received by a previously aligned detector.

Referring again to FIG. 6A, in a next step 605, communication module 533 may receive a signal from alignment adjustment computer 501, collimator computer 531 (for example via interactive display 511, or user device 510 indicative of initiation of an alignment x-ray exposure. In response to receiving the signal, in a next step 606, position calculator 505 may compute a location of radiation beam, received from portable radiation source 530, and striking detector 520. Further, in a next step 607 position calculator 505 may determine whether location of the radiation beam is aligned to a center of detector 520.

In an embodiment, if a determination is made by position calculator 505 that radiation beam is not aligned to the center of detector 520, in a next step 610, shutter controller 532 may readjust shutters 540, until the radiation beam is aligned to the center of detector 520. Otherwise, in a next step 609, shutter controller 532 may adjust the size of shutters 540 such that collimated area of collimator 538 is set to a size of an anatomic region to be examined (for example, area 805 referring to FIG. 8A). In a next step 611, interlocker 506 may deactivate the x-ray interlock to allow radiation from radiation source 530 to complete the x-ray procedure. Further, referring again to step 608, if collimator computer 531 determines the type of exposure that detector 520 is exposed to as radiographic imaging, method 600 may continue to step 609, wherein shutter controller 532 may adjust the position of shutters 540 such that collimated area of collimator 538 is set to a size of an anatomic region to be examined (for example, area 805 referring to FIG. 8A).

In step 612, border detection module 507 may continuously monitor a border condition whereby if a border 1201 or border 1204 (referring to FIGS. 12B and 12C) is activated, shutter controller 532 may again adjust the position of shutters 540 such that radiation may no longer activate border pixels within border 1201 (i.e. radiation is within area 1202). The border condition and detection are further described in FIG. 6B.

Figure 6B:
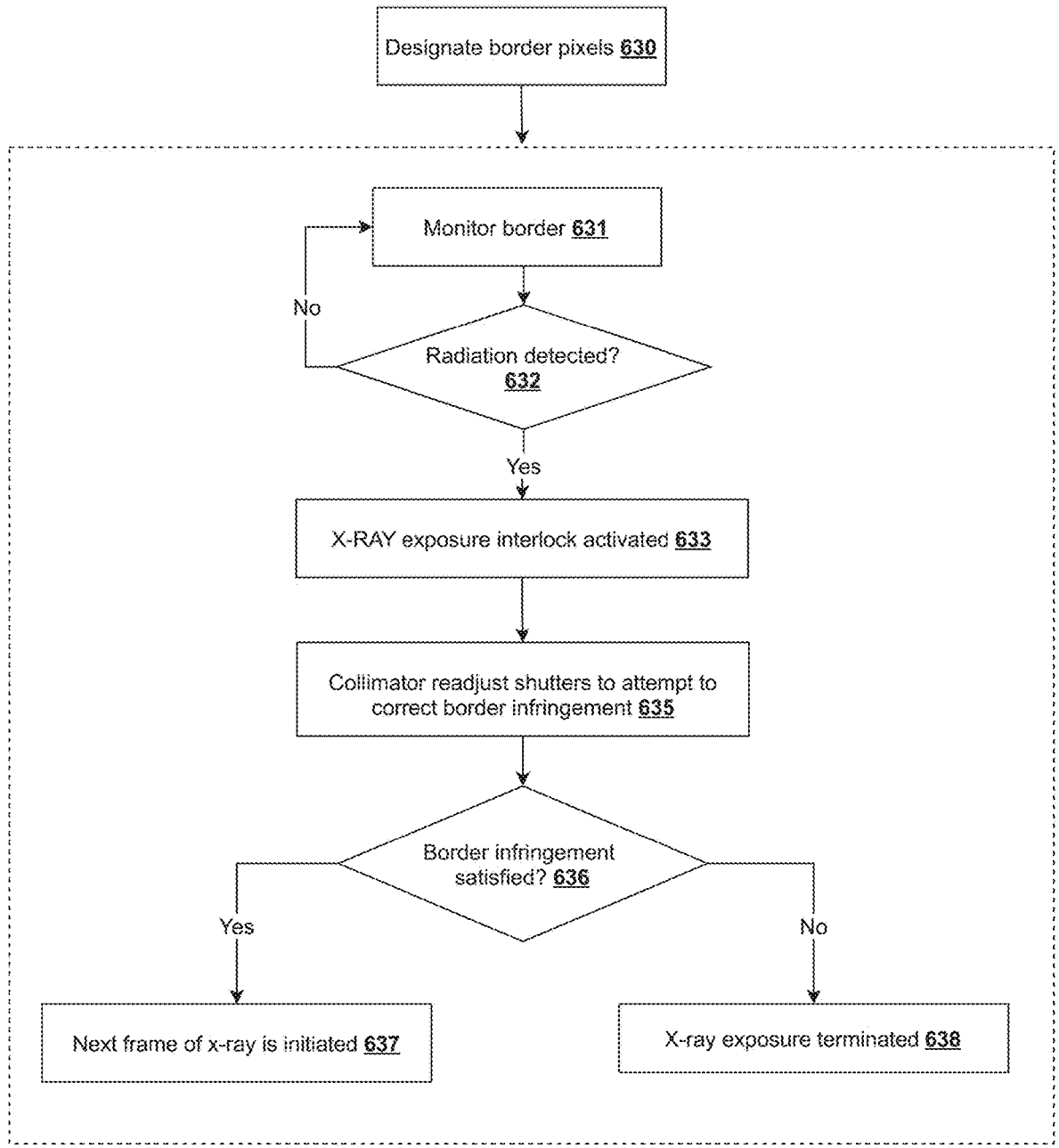
FIG. 6B illustrates an exemplary method for border detection, in accordance with a preferred embodiment of the invention.

FIG. 6B illustrates an exemplary method for border detection for detector 520, in accordance with a preferred embodiment of the invention. According to the embodiment, at a first step 630, border pixels for detector 520 are designated by position controller 504 by a pre-configuration defining area 1201 (referring to FIG. 12B) or by a separate border module 1204 (referring to FIG. 12C). In a next step 631, border detection module 507 may monitor one or more borders 1201 of detector 520. Further, in a next step 632, border detection module 507 may determine whether radiation is detected at the one or more borders. In an embodiment, collimator computer 531 may analyze each frame of image data to determine if an exposed area of detector 520 activated any border pixels of the one or more borders (i.e., exposes a predefined area 1201 or 1204 of pixels on any outer edge of detector 520). In an embodiment where the detected radiation is such that the exposed area overlaps one or more borders of detector 520, in a next step 633, an x-ray exposure interlock is activated by interlocker 506. Otherwise, border detection module 507 may continue to monitor the one or more borders of detector 520 during, for example, a fluoroscopic procedure.

Further, in the instance where detected radiation on the exposed radiation infringes upon one or more borders of detector 520, in a next step 635, shutter controller 532 may adjust shutters 540 in an attempt to correct the detected border infringement. Such an adjustment may be communicated to position controller 504 which may adjust a position of the shaded area on interactive display 511, that is, position controller 504 may continuously ensure, in an embodiment, that the collimated area of collimator 538 shall always mirror the position represented by the shaded area within interactive display 511. In a next step, border detection module 507 may determine whether border infringement is satisfied. If border infringement is satisfied, a next frame of radiation may be initiated by collimator computer 531. Otherwise, radiation exposure may be terminated in a next step 638.

In an embodiment, image acquisition remains enabled when border infringement is satisfied, and the next frame of x-ray exposure is acquired by collimator computer 531. However, if the exposed area approaches or activates pixels within any of the one or more borders of detector 520, position controller 504 may attempt to reposition the radiation beam towards a center position of detector 520. In case where the repositioning of the radiation beam does not satisfy the border infringement due to the mechanical limitations of collimator 538, then a radiation exposure termination command may be sent by alignment adjustment computer 501 to collimator computer 531. In some embodiments, an override switch (not shown) may disable the border detection process 612 at any time before, during or after a procedure.

Figure 7:
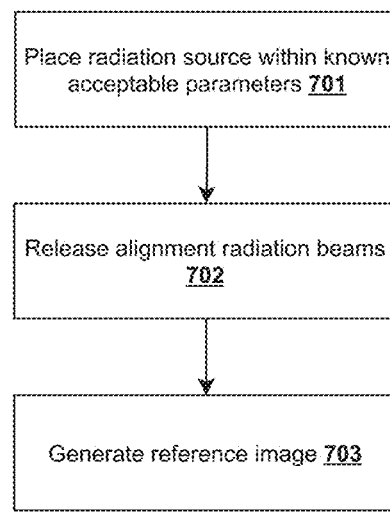
FIG. 7 is a flow diagram illustrating a method for creating a reference image according to a preferred embodiment of the invention.

FIG. 7 is a flow diagram illustrating a method for creating a reference image according to a preferred embodiment of the invention. According to the embodiment, an x-ray system comprises a device used to generate x-rays used to acquire an x-ray image of an object that can also be can used for the common x-ray uses including sterilization, fluorescence, medical and diagnostic purposes. Typically, it would allow one to take images or video in a single, pulse, or continuous emission exposure from many degrees of freedom for use with a portable detector 520.

A portable detector 520 may be a freely movable system may receive x-rays that converts X-ray photons received on its surface to lower energy photons, and subsequently to electric signals, which are acquired and processed to reconstruct an image of features within a subject.

In some embodiments, a collimator may adjust a beam size to a desired size for imaging a desired area by narrowing radiation beam that can function to create an alignment beam aperture, and/or narrow the beam for other imaging purposes In some embodiments, one or more positioning plate between the portable radiation source and the portable detector system 520 may block most radiation except for the positioning aperture which constrains the beams to form an alignment beam.

In some embodiments herein termed the "collimator hole in shutter blades" embodiment, the "incomplete closed collimator" embodiment, the "positioning aperture plate" embodiment, and the "low dose system" embodiment wherein the "collimator hole in shutter blades" embodiment comprises an embodiment where the collimator has holes in the shutter blades that are the source of the radiation alignment radiation beams, the "incomplete closed collimator" embodiment comprises an embodiment where the collimator does not have holes in the shutter blades, but rather generates an alignment radiation beams by having an incomplete closure of the collimator shutter blades, the "positioning aperture plate" embodiment comprises one or more configurable plates that serves to limit most or all exit radiation from the radiation source, except for those through the alignment beam holes, thereby generating a radiation alignment radiation beams, the "low dose system" comprises an embodiment where the alignment radiation beams are created by a portable radiation system capable of emitting a low dose alignment radiation beam.

To create a reference or alignment image, the radiation source system is placed within known acceptable spatial parameters of the portable detector 520 in step 701 wherein the size of the portable detector 520 is known as is the size of the maximum, minimum, and desired collimated area of the collimator. In a next step 702, alignment radiation beams are then released through one or more positioning aperture used for aligning the portable radiation source and the portable detector 520. Upon the alignment beams striking the portable detector 520, in a next step, 703, a reference image is generated.

The reference image comprises an image, which may be radiographic or fluoroscopic, may be associated with other alignment information data operably connected to a computer and stored in memory in order to determine alignment of detector 520 to x-ray source, e.g., at, for example, the time of manufacture and assembly.

It should be appreciated that a reference image when used with a procedure image may be used to facilitate calculations of source image distance (SID) and orientation of radiation source relative to detector and may be used with subsequent imaging procedures to identify differences, sizes, distances, and the like. With system 500 recognizing SID and SOD, other calculations may be performed such as determining object thickness.

By using previously captured reference images, subsequent images with known information (for example, size of detector), a virtual border 802 may be programmatically calculated by border detection 507. A virtual border may then be used to detect a border infringement condition.

In some embodiments, visual indicia may be displayed to notify a user, via interactive display 511 (referring to FIG. 5), that an area 805 (referring to FIGS. 8B-8C) may be approaching a virtual border 802, for example, by coloring an approached border on interactive display 511 (i.e. display 801), playing a sound, or some other indicator.

Figure 8A:
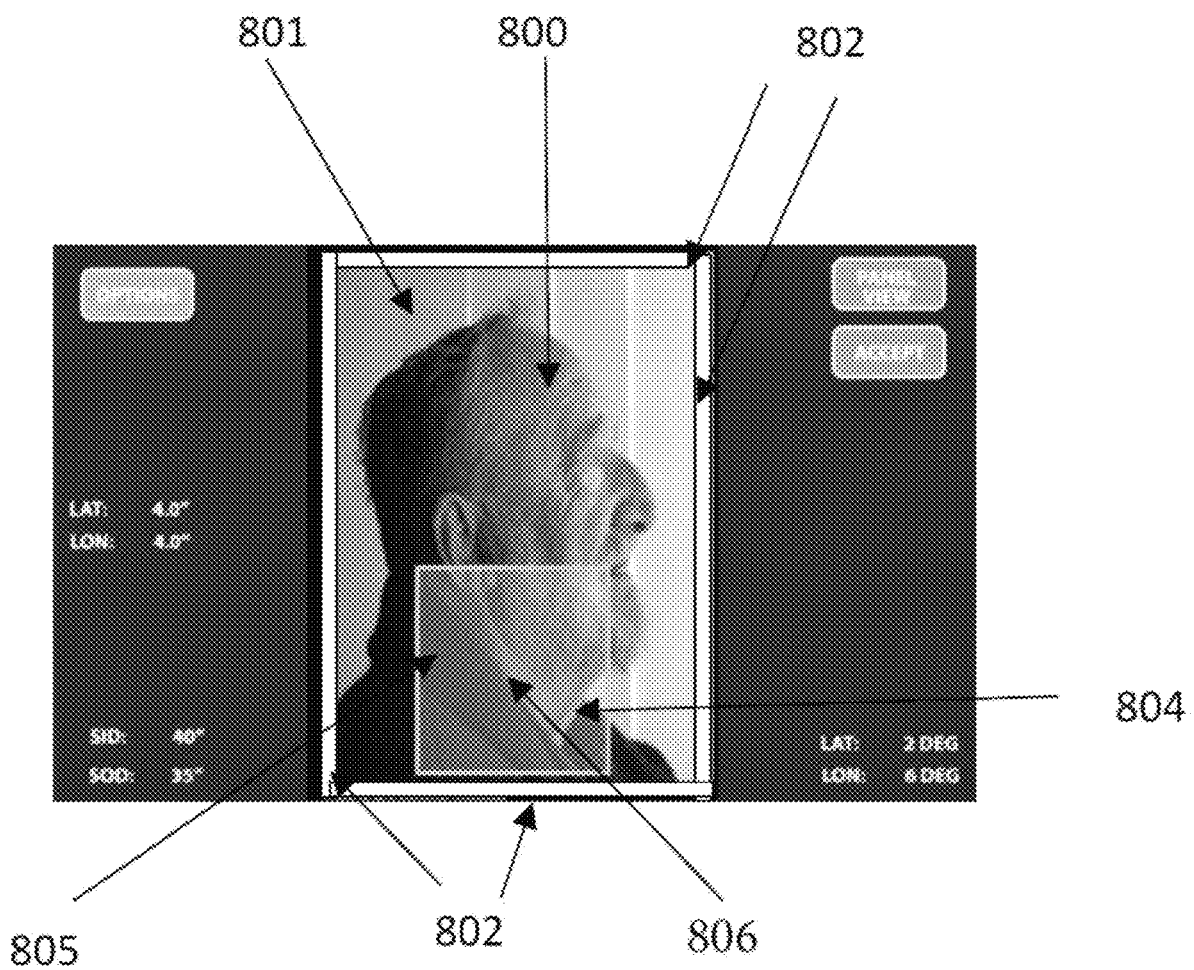
FIG. 8A illustrate an exemplary interactive display for receiving FOV images and for providing input by a user, according to a preferred embodiment of the invention.
Figure 8B:
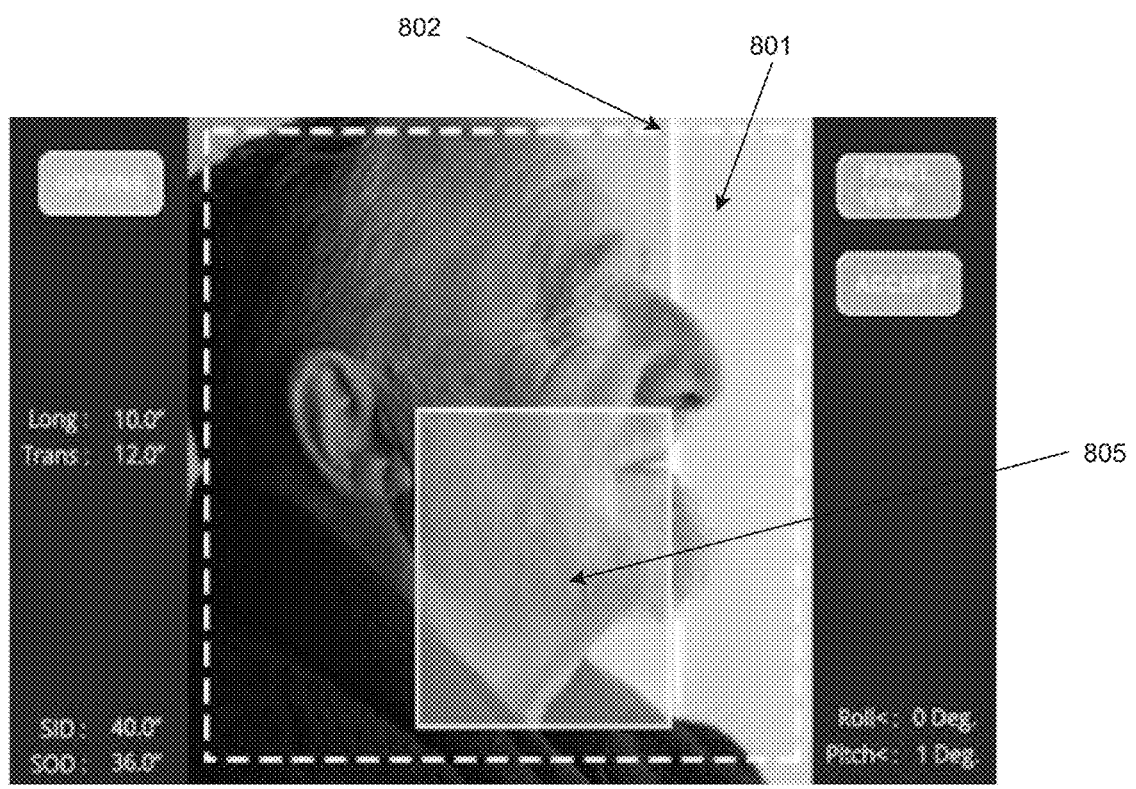
FIG. 8B-8C are illustrations representing an image with a virtual border corresponding to a portable detector, according to a preferred embodiment of the invention.
Figure 8C:
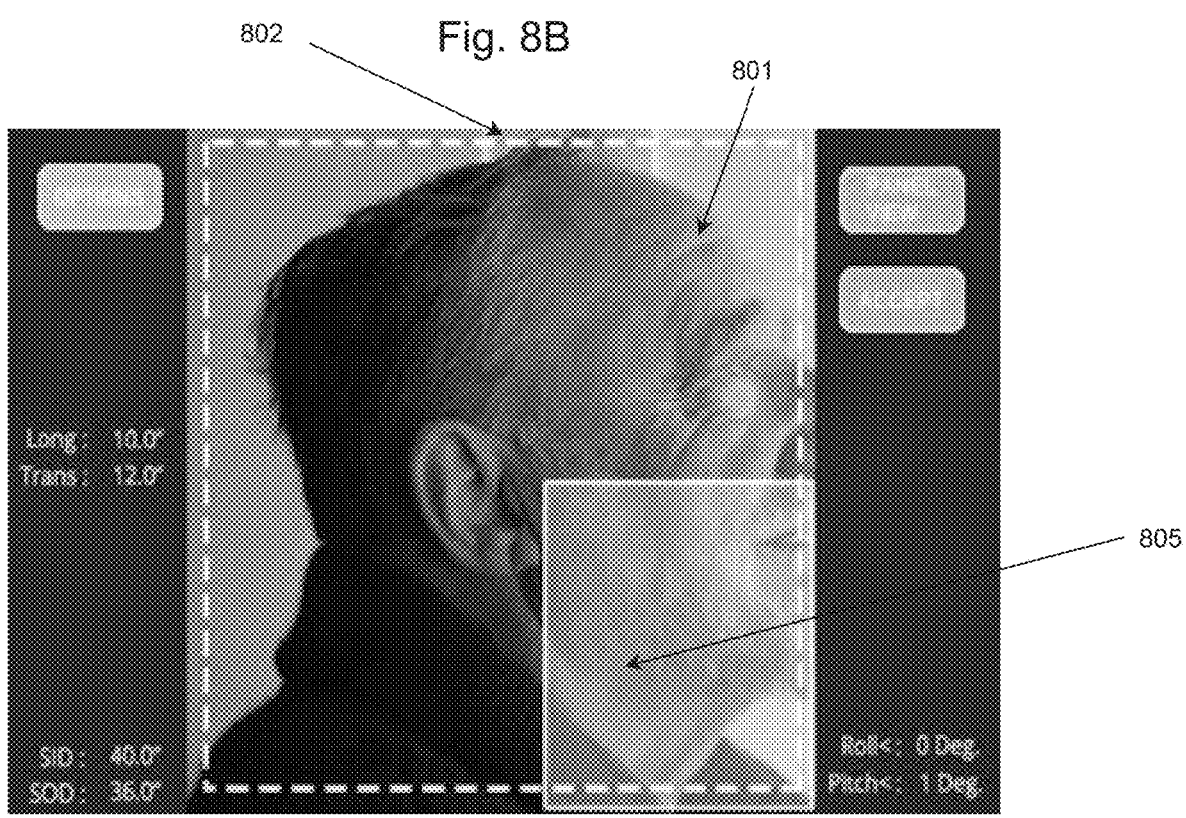
Figure 8D:
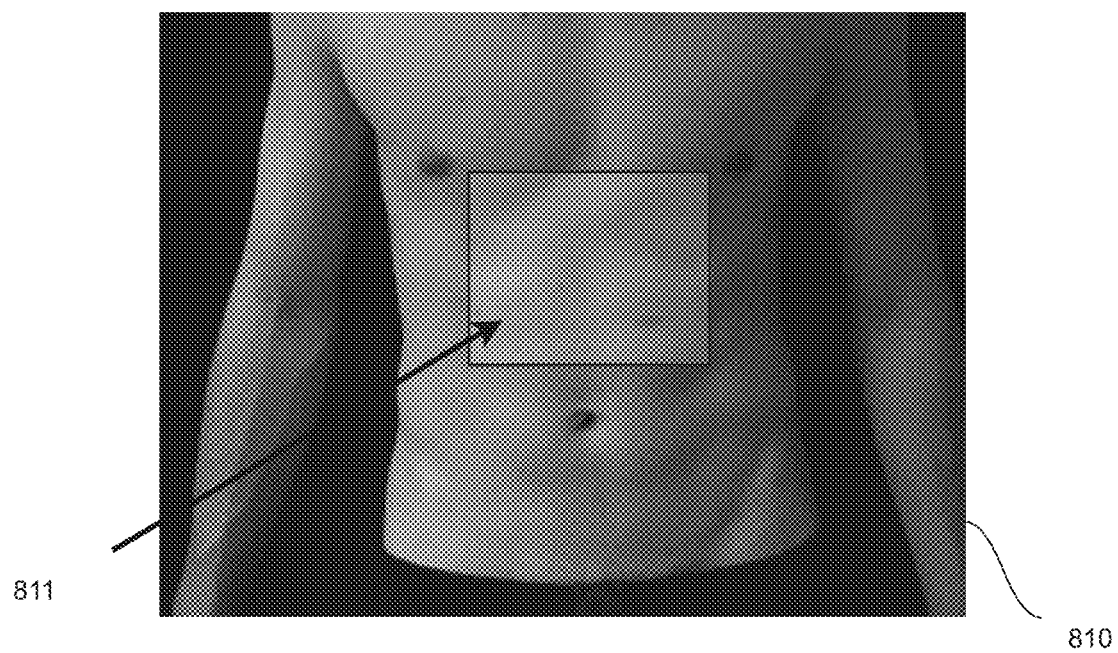
FIG. 8D are images illustrating a field of view of a patient with a region of interest, according to an embodiment of the invention.
Figure 8E:
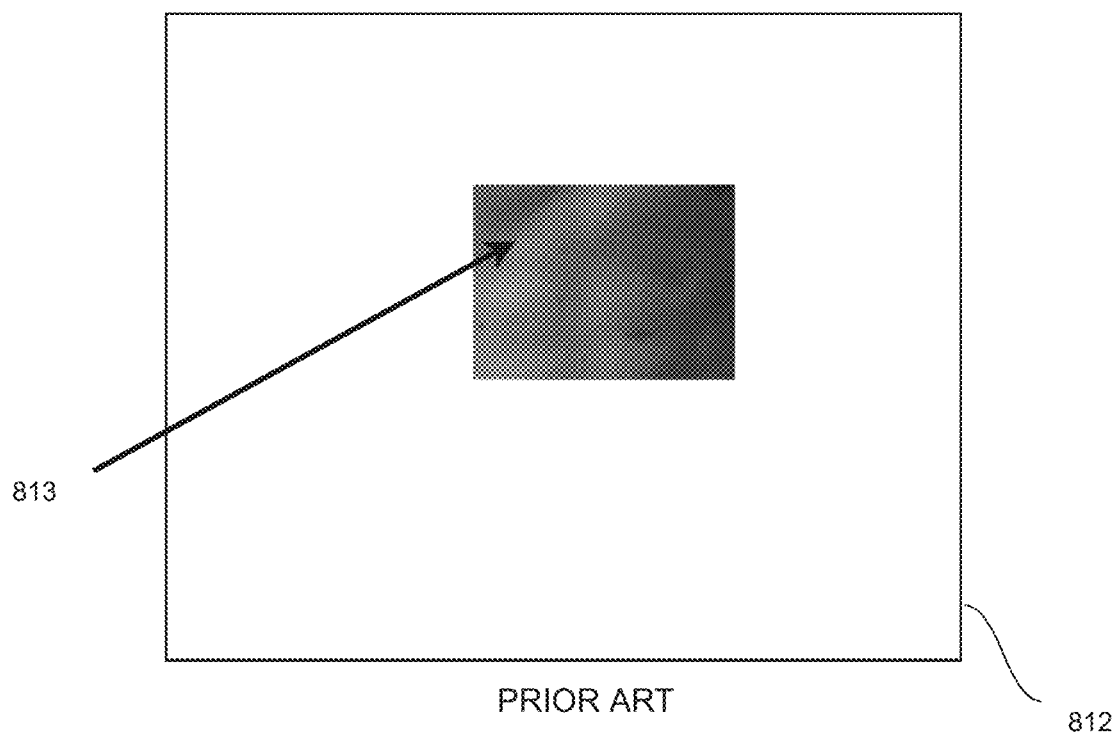
FIG. 8E are images illustrating a field of view of a patient with a region of interest, according to systems known in the art.

FIGS. 8A-C illustrate exemplary detector surface configurations, according to a preferred embodiment of the present invention. For the sake of brevity and conciseness, portable radiation source 530 is said to be aligned with detector 520 when the radiation beam exposes a portion of detector 520 surface within a pre specified limit. However, a person skilled in the art may recognize that several other portions of detector 520 surface may be considered as target for the radiation beam to satisfy one or more medical imaging needs.

As depicted in FIG. 8A, interactive display 511 may camera image 800, for example as captured by camera 1108 (referring to FIG. 11A) which may be representative of an exemplary image of a patient undergoing an imaging procedure. Camera images of the patient may be representative of an active area of detector 520 when exposed to one or more radiation beams received from portable radiation source 530. Further, in some embodiments, the camera images may further comprise of a shared, blurred, or other shaded area 805 within the camera images, that may be indicative of a specific anatomical part of the patient under study. In the embodiment shown in FIG. 8A, the camera image may show the patient's face and the shaded area may concentrate on the buccal area 804 of the patient. It should be noted that camera image 800 (that is, an image obtained from camera 537) may coincide to a position and a usable area of detector 520. The shaded area may coincide to the position and location of the radiation beam.

In an embodiment, resizing and movement of the shaded area may be transmitted by collimator computer 531 to move the collimator shutters to pattern a collimated x-ray to corresponding location on detector 520. In some embodiments, interactive display may be a smartphone, mobile device, tablet device, PDA device, or any other device having an interactive display. In a preferred embodiment, a user, such as an operator or radiologist, may be able to readjust the shaded area over the camera image. The shaded area may be readjusted using any conventional technique, such as pinch-to-zoom, or other multi-touch or gesture-based techniques. directly to interactive display 511 whereby the camera image 800 can be manipulated (for example, to resize area 805.

FIG. 8B is another illustration depicted in FIG. 8A whereby a virtual border area 802 is represented in accordance with an embodiment of the present invention. In the given configuration, area 805 which represents a collimated area of collimator 538 lies within border area 802. In such configurations whereby the collimated area is within the area defined by border area 802, interlocker 506 may disengage interlock to allow radiation, by radiation source 530, to be targeted at detector 520. In some embodiments, alignment adjustment computer 501 may transmit a repositioning signal to collimator computer 531 based on one or more user input received from interactive display 511 whereby area 805 may be graphically repositioned or resized by the user. In an example, the repositioning signal may include commands for collimator computer 531 to modify aperture size via movements of collimator shutters, 540 and location for a collimated area of collimator 538. Further, collimator computer 531, based on the received aperture size and location in the repositioning signal, may actuate shutters 540 to change the size and position of the radiation beam striking surface of detector 520. Once the position of the radiation substantially matches a predetermined position, e.g., centered to detector surface, interlocker 506 may disengage the interlock to allow radiation to strike detector 520 at the predetermined position. In some embodiments, the aperture size and position may be modified based on movement of shutters 540, and the radiation beam may now strike detector 520 surface in a position of detector 520 based on the collimated area associated to the shutter positions.

FIG. 8C illustrates a border infringement condition in accordance with an embodiment of the present invention. According to the embodiment, image 805, as seen by the FOV of camera 1102 (and, in turn, the collimator assembly), may indicate that an activation of border pixels within border 802 may be present, or in some embodiments, activation, or proximity to a virtual border represented by borders 802. Accordingly, border detection procedure outlined in FIG. 6B would be followed. It should be noted that system 500 may function equally with a computer virtual border 802 or via receiving communication from portable detector 520 indicating that pixels have been activated by radiation.

Figure 9:
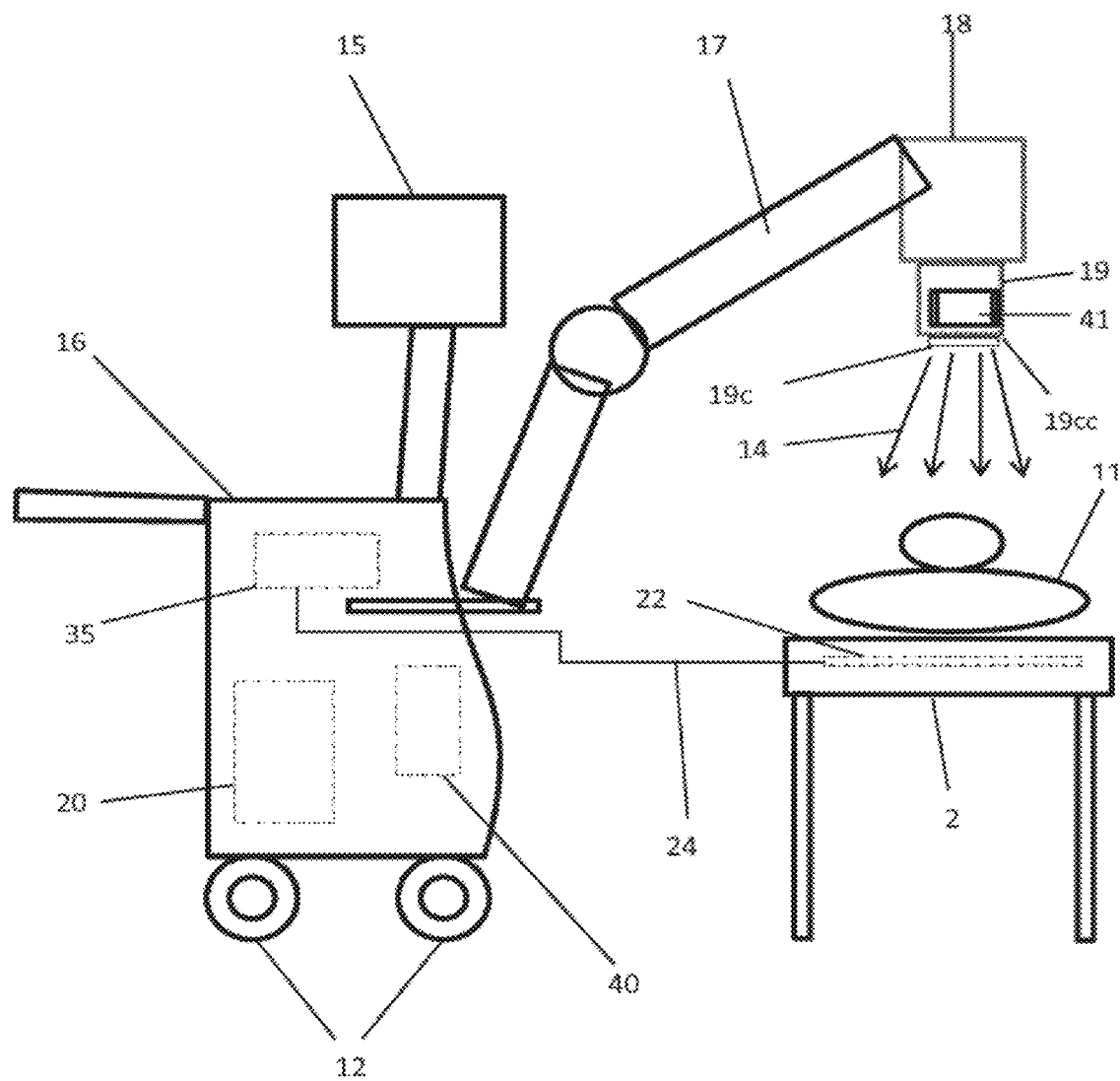
FIG. 9 is block diagram illustrating a system for mobile imaging, according to a preferred embodiment of the invention.

FIG. 9 is block diagram illustrating a system for mobile imaging, according to a preferred embodiment of the invention. According to the embodiment, a mobile radiation imaging system is presented, referenced generally by reference numeral 16. In the illustrated embodiment, the mobile radiation imaging system 16 may be a digital radiation system that is designed both to acquire radiographic and/or fluoroscopic image data and to process the image data for display in accordance with the present techniques. In particular, system 16 is operable to produce both radiographic images and/or fluoroscopic images.

In a preferred embodiment, mobile imaging system 16 generally comprises a mobile cart having caster wheels 12, a portable radiation source 18, operatively attached to a manipulatable arm 17 and capable of moving in all degrees of freedom, and a portable flat-panel digital radiation detector 22. Importantly, portable radiation source 18 is capable of producing both radiographic (via single radiation emissions) and fluoroscopic radiation images (via pulse or continuous radiation emissions). Detector 22 is capable of acquiring both radiographic (via single radiation emissions) and fluoroscopic radiation images (via pulse radiation emissions). Imaging system 16 also comprises a collimator 19 positioned adjacent to the portable radiation source 18 which permits a controlled stream of radiation 14 to pass into a region in which a patient 11 is positioned on table 2. An aperture ensures that the stream of radiation 14 is the correct size for the detector 22 further described below. A portion of the radiation 14 passes through or around the subject and impacts detector 22. The detector 22 converts photons received from the radiation on a surface of detector 22 to lower energy photons, and subsequently to electric signals, which are acquired and processed by the system computer to reconstruct an image of the features within the subject.

As can be appreciated from FIG. 9, alignment between portable radiation source 18 and detector 22 is of critical importance. If portable radiation source 18 and detector 22 are not aligned, the portion of radiation 14 that passes through or around the subject cannot be received by detector 22, and an accurate image of the subject therefore cannot be obtained. Furthermore, even if detector 22 is directly in line with portable radiation source 18, detector 22 must be oriented such that its plane is perpendicular to portable radiation source 18 for proper detection of radiation 14. In one embodiment, once the precise alignment is realized, interlock 20 may be disengaged, such that user may proceed with the imaging procedure. Further, in case portable radiation source 18 misaligns with detector 22 (for example, by activation a border condition), interlock 20 may again be activated and a signal to portable radiation source 18 may be transmitted to pause transmission of radiation beams, thereby reducing the risk of over exposure of the subject to radiation.

In an operating configuration, the subject is positioned on table 2 and located between portable radiation source 18 and detector 22. Detector 22 can be coupled via wirelessly or via data cable 24 to system computer 35) which commands acquisition of the signals generated from detector 22, although wireless communication between detector 22 and alignment computer 35 is the more preferred method. As the detector receives radiation 14 that may pass through the subject, imaging data is transmitted to system and alignment adjustment computer 35 (also referred to herein as alignment adjustment system 501).

In most cases, system computer 35 may also execute various signal processing and filtration functions, such as for initial adjustment of dynamic ranges, interleaving of digital image data, and so forth. Further, system computer 35 also enables a user to control the operation of mobile imaging system 16 to produce a desired image. Images processed by system computer 35 may be displayed on a monitor 15. Electrical power for portable radiation source 18, collimator 19, and detector 22 may be provided by a conventional AC/DC power supply 25 that may be located within the cart, and which may be electrically connected to any available power source.

Because movement of detector 22 is independent of portable radiation source 18, it may be possible for radiation 14 to strike detector 22 at an angle or not centered to detector 22 producing inaccurate images of the subject. Further, alignment adjustment computer 35 may send processed data pertaining to orientation and position of portable radiation source 18 to display 41. The data received by LCD display 41 may visually display the orientation and location of detector 22 with respect to portable radiation source 18.

Alignment between the portable radiation source 18 and the detector 22 and size of stream of radiation 14 is of critical importance. If the portable radiation source 18 and the detector 22 are not aligned, a portion of the stream of radiation 14 may not pass through the patient 11 at the intended position, orientation or angle, so the stream of radiation 14 cannot be properly received by the detector 22, and an accurate image of the patient 11 cannot be obtained. Furthermore, even if detector 22 is directly in line with portable radiation source 18, detector 22 should be oriented such that its plane is perpendicular to portable radiation source 18 for proper detection of radiation 14. In addition, for fluoroscopic procedures, alignment and stream of radiation 14 must conform to regulatory standards of alignment of the radiation stream size of portable radiation source 18 to detector 22. That is, if portable radiation source 18 is not within the alignment tolerance, or stream of radiation 14 is not of the proper size, mobile imaging system 16 must inhibit portable radiation source 18 from producing radiation 14. The tolerances may vary but will typically be 2% of the distance between portable radiation source 18 and detector 22 (given by source image distance, SID). The predetermined alignment conditions of this invention also may vary, but typically in the United States, for example, will be one or more of SID is usually set at 40 inches, (40 inches× 0.2=0.8 inches total), i.e., portable radiation source 18 and detector 22 cannot be more than 0.4 inches off the center axis.

Alignment of a portable radiation source and a portable detector are outlined in U.S. Pat. Nos. 9,788,810, 9,693,746, and 10,918,347 which are hereby incorporated by reference.

Figure 10:
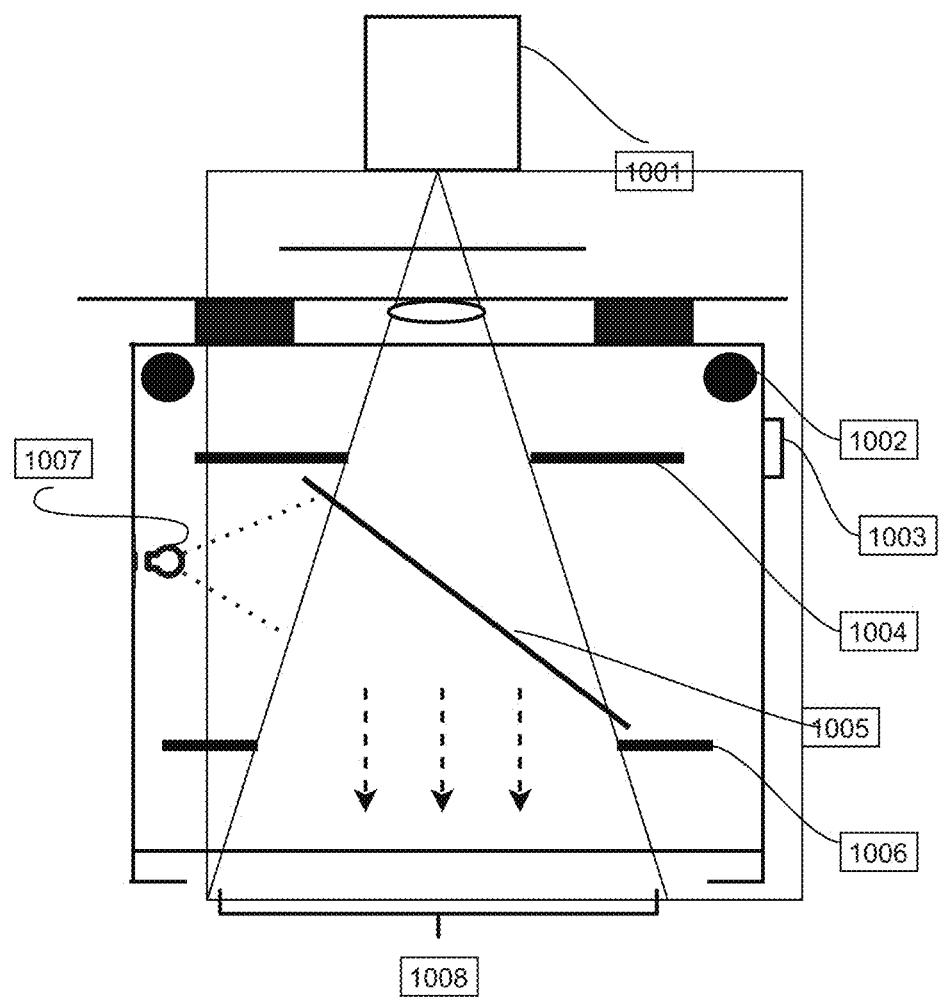
FIG. 10 illustrates a conventional light source and mirror arrangement for imaging, in accordance with systems known in the art.

FIG. 10 illustrates a conventional light source and mirror arrangement for imaging, in accordance with systems known in the art. Current conventional collimators provide a high intensity light source 1007 and a mirror 1005 in order to comply with FDA requirements. The conventional light source and mirror arrangement may further include an upper set of diaphragms, as represented by diaphragm 1004 and a lower set of diaphragms, as represented by diaphragm 1006.

Further, one or more control knobs, represented by control knob 1002 may also be provided in order to control the upper diaphragms 1004 and lower diaphragms 1006. In general, such control knobs 1002 may be used to open and close the set of diaphragms 1004, 1006, in order to set a path for radiation beams that are received from x-ray source 1001 during an imaging process. Furthermore, a light switch 1003 may also be provided to control the workings of high intensity light source 1007.

As shown in FIG. 10 light from high intensity light source 1007 is reflected by mirror 1005 through collimator shutter aperture (not shown) as represented by the set of dotted arrows. The reflected light may project a light field representative of the size and location 1008 of the radiation beam on the patient or object, as shown in the figure.

Disadvantages of a light source and mirror assembly, such as that described in FIG. 10 may include increase in size and weight of the collimator. Such an increase in the weight of the collimator may be undesirable for use with mobile of portable imaging systems. Further, the high intensity light source 1007 commonly used must be compliant with FDA regulations, especially FDA CFR 1020 (2) (ii), that states, "when a light localizer is used to define the x-ray field, it shall provide an average illuminance of not less than 160 lux (15 foot candles) at 100 centimeters or at the maximum SID, whichever is less". This is especially disadvantageous when the imaging procedure consists of pediatric or neonatal patients, due to a possibility of high intensity light directed into the patient eyes causing discomfort and/or injury. Further, the light source mirror assembly does not project precisely define light field edges on the patient or object, making it difficult for a user to precisely adjust the radiation beam size and location for the anatomic region being examined. Accordingly, visualizing the light field, by a user, would be especially problematic in bright lighted locations.

Figure 11A:
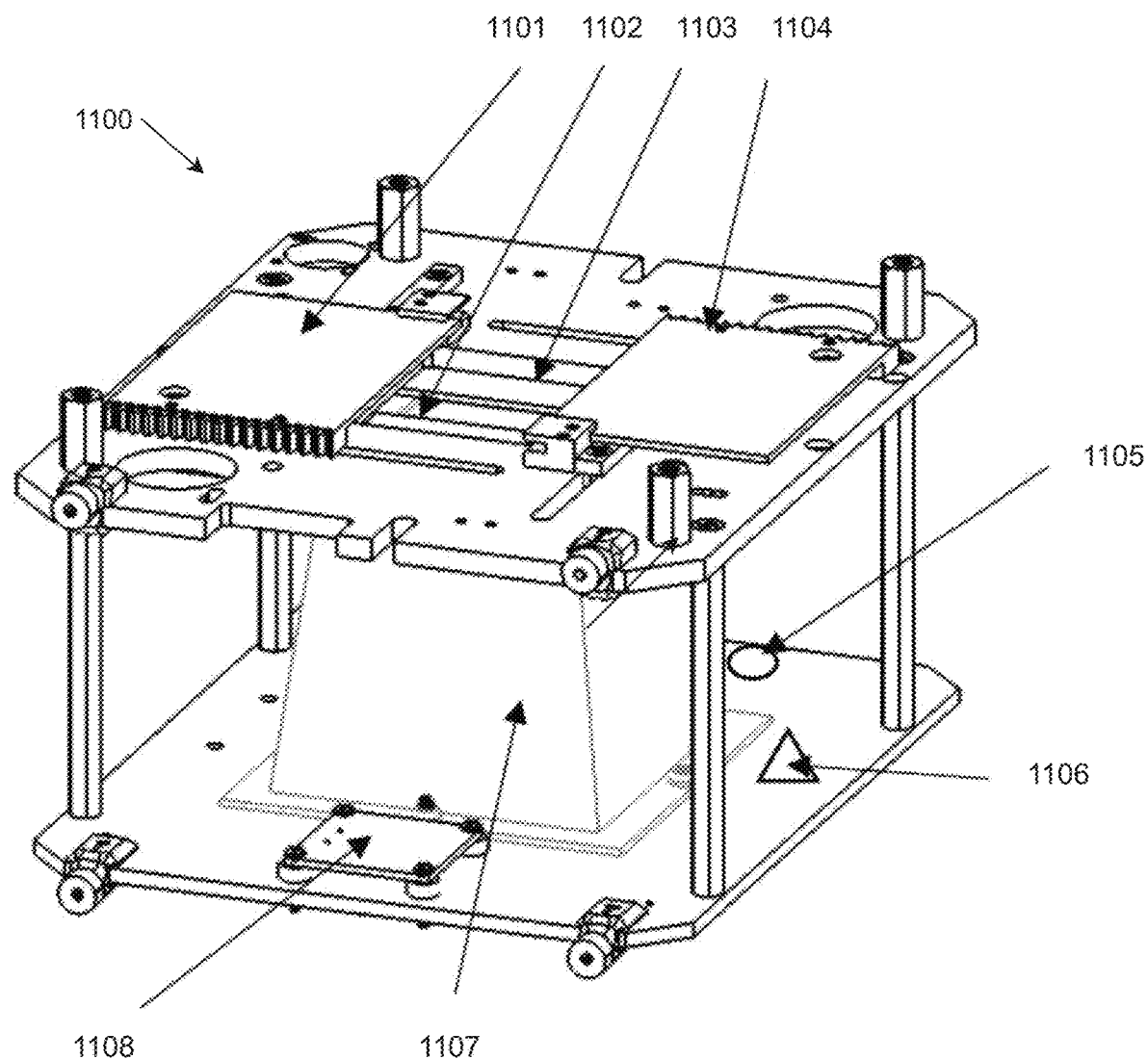
FIG. 11A-11D illustrate components of a motorized collimator, according to a preferred embodiment of the invention.

FIG. 11A is an illustration of a motorized radiation beam collimator, according to a preferred embodiment of the invention. According to the embodiment motorized collimator 100 comprises one or more shutters 1101, 1102, 1103, and 1104 (collectively referred to as shutters 540) forming an aperture in the middle; camera 1108; an x-ray source to object (patient) measuring device 1106 to measure source to object distance (SOD); IMU 1105 may comprise one or more devices to measure tilt, angulation, rotation, etc.

Metallic barrier cone 1107 may be used to diverge and limit radiation beams from a point source associated to radiation source 530 to the calculated size of the detector active area. Advantageously a cone shape for metallic barrier cone reducing a volume of irradiated to the size of the detector. Further, but not requiring a metallic housing for light source and mirror arrangement (as is required in systems known in the art), weight of the head unit is advantageously decreased resulting in a portable radiation system with a lower weight, lower center of gravity, and more portability.

Figure 11B:
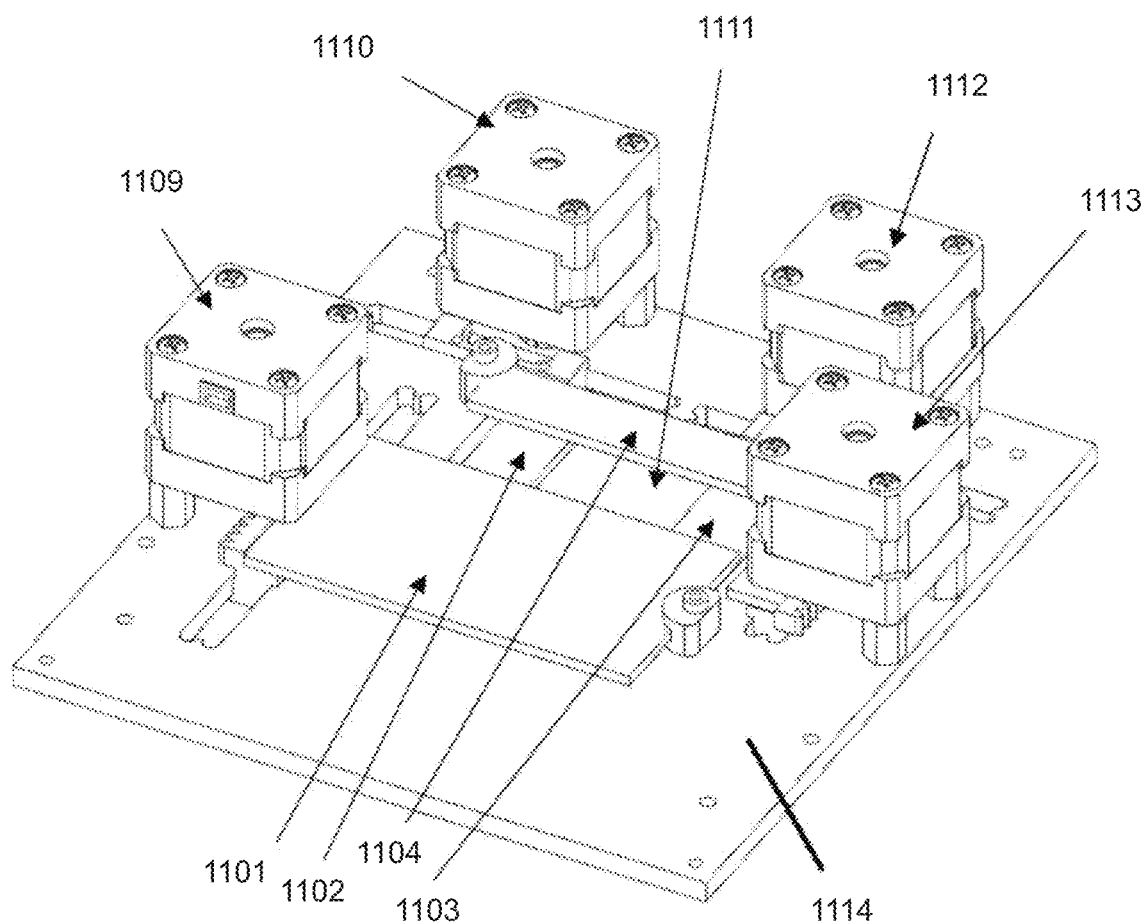

FIG. 11B is an illustration of a motorized radiation beam collimator, according to a preferred embodiment of the invention. According to the embodiment, a motorized radiation source beam collimator comprises four independents internal shutters that are independently adjustable via four independent motors 1109, 1110, 1112 and 1113 operable to shape beams of radiation emerging from a radiation source to adjust field size and position of a beam, via variable positions of one or more shutters 1101, 1102, 1103, and 1104 (collectively referred to as shutters 540). The motors, in communication with the collimator computer 531, may be automatically adjusted to move one or more shutters 540 to only allow a small alignment radiation beam to strike the detector 520 pixels through aperture 1111, the collimator computer 531 comprising a memory, a processor, and a plurality of programming instructions, the plurality of programming instructions when executed by the processor cause the processor to establish communication with the detector comprising a pixel grid pattern of a location of a plurality of pixels, the collimator computer 531 may calculate a position of the radiation source relative to the detector from data receive from the detector pertaining to the locations of at least a portion of the pixels that are activated, on detector 520, by a quantity or an intensity of alignment radiation beams from the radiation source. The independent movement of the one or more collimator shutters 540 allow the collimator computer 531 to maintain an alignment of the radiation beam to the detector. In this regard, shutters 540 and collimator computer 531 may realign the radiation beam upon the radiation source no longer being aligned to the detector due to, for example, intended or untended movement of the radiation source or portable detector.

Accordingly, collimator computer 531 may adjust the independent shutter to realign the radiation beam to detector 520, via motors 1109, 1110, 1112 and 1113. Alignment computer 531 may further alert an operator via alignment adjustment computer 501 or via user device 510, that an imaging area is approaching the detectors outer border due to the size of the image or movement of the radiation source and/or detector. The collimator computer 531 may then readjust, via motors 1109, 1110, 1112 and 1113, the image size or realign the image to the center of the detector.

Figure 11C:
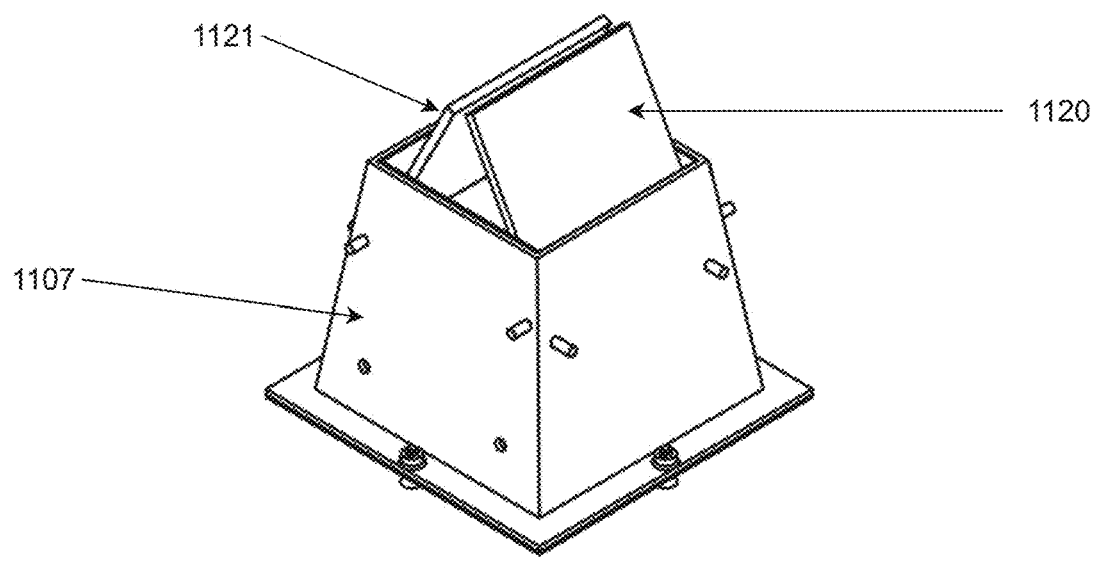
Figure 11D:
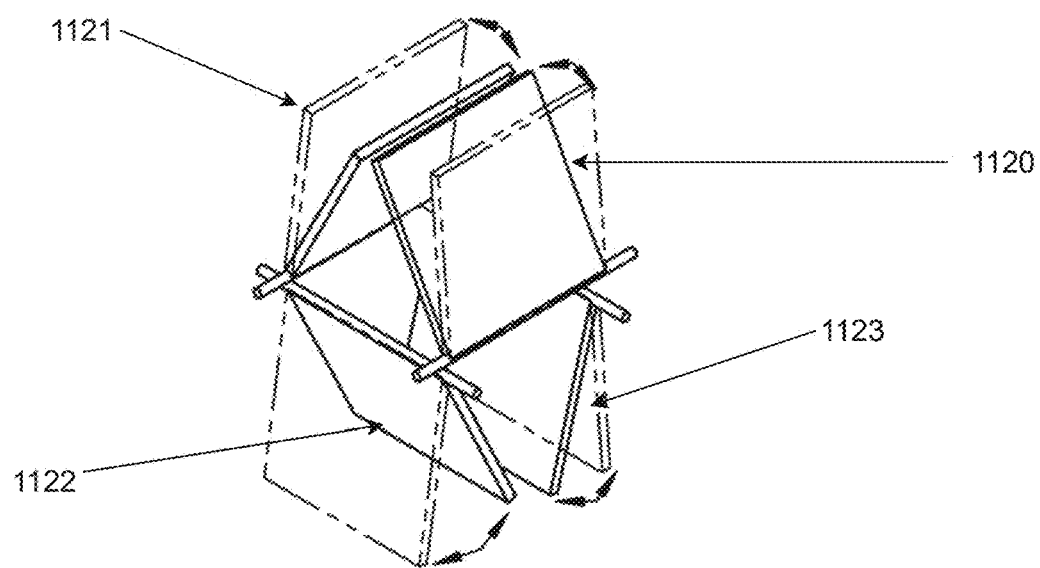

FIGS. 11C and 11D are illustrations of a collimator cone according to some embodiments of the invention. According to the embodiments, cone 1107 may comprise movable plates 1120, 1121, 1122, and 1123 whereby movements of the plates may be performed by one or more motors (not shown) in a similar fashion using the same systems and methods disclosed herein to move shutters 1101, 1102, 1103, 1104 to control the size, shape and amount of radiation through an aperture between movable plates 1120, 1121, 1122, and 1123. It should be appreciated that movable plates 1120, 1121, 1122, and 1123 are operable to manipulate radiation in the same, or similar, fashion as described in FIG. 11B.

FIG. 12A is a block diagram illustrating portable detector 520, according to an embodiment of the invention. According to the embodiment, freely movable detector 520 receives x-ray photons on surface 1202 and may convert them to lower energy photons, and subsequently to electric signals, which are acquired and processed to reconstruct an image of the features within the patient. The image may then be communicated to a computer via a communication module.

FIG. 12B is a block diagram illustrating portable detector 520 comprising an area designated as a border detection area. According to the embodiment, area 1201 comprises a subsection of area 1202 that may be preconfigured to identify when radiation has activated pixels within area 1201. Accordingly, steps may be taken to notify a computer that pixels were activated signaling a border infringement condition.

FIG. 12C is a block diagram illustrating portable detector 520 comprising an area designated as a border detection area that is a separate component of detector 1202. According to the embodiment, component 1204 may be a separate device operable to detect radiation in order to communicate a border infringement condition.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The skilled person will be aware of a range of possible modifications of the various embodiments described above. Accordingly, the present invention is defined by the claims and their equivalents.

What is claimed is:

1. A collimator control system for fluoroscopic procedures, comprising:
   a collimator comprising a plurality of motorized shutters, the collimator communicatively connected to a network-connected alignment adjustment computer, the plurality of motorized shutters controllable via the network;
   the network-connected alignment adjustment computer comprising a processor, an interactive display, a camera, a memory, and a plurality of programming instructions, the plurality of programming instructions when executed by the processor cause the processor to:
   receive an image from the camera;
   display the image on the interactive display, the image comprising a shaded area, the shaded area corresponding to a collimated area of the collimator;
   recursively receive one or more adjustments from the interactive display, the adjustments corresponding to a change in size of the shaded area or a change in position of the shaded area, or both;
   upon the location of the collimated area not corresponding to a location represented by the shaded area, adjust the collimated area by adjusting the plurality of shutters to correspond the location represented by the shaded area; and
   upon the size of the collimated area not corresponding to a size represented by the shaded area, adjust the size of the collimated area by adjusting the plurality of shutters to correspond to the size represented by the shaded area.

2. The system of claim 1, wherein the plurality of programming instructions when further executed by the processor cause the processor to:
   communicatively connect to a portable detector;
   continuously monitor a border infringement condition, the border infringement condition determined by activation, by a radiation source, of at least a portion of a plurality of border pixels, the at least a portion of the plurality border pixels comprising a predefined plurality of pixels comprised within, or adjacent to, the portable detector;
   wherein each pixel of the plurality of pixels is operable to be activated by an intensity of radiation from the radiation source.

3. The system of claim 2, wherein one or more characteristics of the portable detector are preconfigured and the plurality of programming instructions when further executed by the processor cause the processor to receive, from a database, the preconfigured characteristics at least comprising the size of the portable detector.

4. The system of claim 2, wherein the portable detector is previously aligned to the collimator.

5. The system of claim 1, wherein the plurality of programming instructions when further executed by the processor cause the processor to:
   upon the location represented by the shaded area overlapping a previously configured virtual border, establish a border infringement condition.

6. The system of claim 5, wherein the previously configured virtual border is calculated based on a size of the portable detector, the previously configured virtual border representing an area substantially around an area representing a perimeter of the portable detector.

7. The system of claim 5, wherein the plurality of programming instructions when further executed by the processor cause the processor to:
   upon the border infringement condition being established, activate the exposure interlock to prevent diagnostic radiation.

8. A computer-implemented method for controlling a collimator for fluoroscopic procedures, the method comprising the steps of:
- communicatively connecting, by an alignment adjustment computer, to a collimator over a network, the collimator comprising motorized shutters controllable via the network;
- receiving, by the alignment adjustment computer, an image from the camera;
- displaying, by the alignment adjustment computer, the image on an interactive display, the image comprising a shaded area, the shaded area corresponding to the collimated area of the collimator;
- recursively receiving, by the alignment adjustment computer, one or more adjustments from the interactive display, the adjustments corresponding to a change in size of the shaded area or a change in position of the shaded area, or both;
- upon the location of the collimated area not corresponding to a location represented by the shaded area, adjusting, by the alignment adjustment computer, the collimated area by adjusting the plurality of shutters to correspond the location represented by the shaded area; and
- upon the size of the collimated area not corresponding to a size represented by the shaded area, adjusting, by the alignment adjustment computer, the size of the collimated area by readjusting the plurality of shutters to correspond to the size represented by the shaded area.

9. The method of claim 8, further comprising the steps of:
- communicatively connecting, by the alignment adjustment computer, to a portable detector;
- continuously monitoring, by the alignment adjustment computer, a border infringement condition, the border infringement condition determined by activation, by a radiation source, of at least a portion of a plurality of border pixels, the at least a portion of the plurality border pixels comprising a predefined plurality of pixels comprised within, or adjacent to, the portable detector,
- wherein each pixel of the plurality of pixels is operable to be activated by an intensity of radiation from the radiation source.

10. The method of claim 8, further comprising the steps of:
- upon the location represented by the shaded area overlapping a previously configured virtual border, establishing, by the alignment adjustment computer, a border infringement condition.

11. The method of claim 10, further comprising the steps of:
- upon the border infringement condition being established, activating, by the alignment adjustment computer, the exposure interlock to prevent diagnostic radiation.

12. The method of claim 9, wherein one or more characteristics of the portable detector are preconfigured and the method further comprising the step of receiving, by the alignment adjustment computer from a database, the preconfigured characteristics comprising at least a size of the portable detector.

13. The method of claim 9, wherein the portable detector is previously aligned to the collimator.

14. The method of claim 10, wherein the previously configured virtual border is calculated, by the alignment adjustment computer, based on a size of the portable detector, and wherein the previously configured virtual border represents an area substantially around an area representing a perimeter of the portable detector.

* * * * *